US009725753B2

(12) United States Patent
Ono et al.

(10) Patent No.: US 9,725,753 B2
(45) Date of Patent: Aug. 8, 2017

(54) BIOMOLECULE INFORMATION ANALYSIS DEVICE

(75) Inventors: Kazuo Ono, Tokyo (JP); Tatsuo Nakagawa, Tokyo (JP); Yoshimitsu Yanagawa, Tokyo (JP); Takayuki Kawahara, Tokyo (JP); Akira Kotabe, Tokyo (JP); Riichiro Takemura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 136 days.

(21) Appl. No.: 14/122,206

(22) PCT Filed: May 31, 2011

(86) PCT No.: PCT/JP2011/062456
§ 371 (c)(1),
(2), (4) Date: Feb. 18, 2014

(87) PCT Pub. No.: WO2012/164679
PCT Pub. Date: Dec. 6, 2012

(65) Prior Publication Data
US 2014/0154790 A1    Jun. 5, 2014

(51) Int. Cl.
*C12Q 1/68* (2006.01)
*G01N 33/487* (2006.01)

(52) U.S. Cl.
CPC ......... *C12Q 1/6802* (2013.01); *C12Q 1/6869* (2013.01); *G01N 33/48721* (2013.01)

(58) Field of Classification Search
CPC ............ C12Q 1/6869; C12Q 2565/631; B01L 3/502761; G01N 27/414; G01N 27/4145; G01N 27/4146; G01N 33/5438; Y10S 977/924; Y10T 436/143333; G01R 17/00; G01R 17/02; G01R 17/10; G01R 17/20; G01R 17/105; G01R 17/12
See application file for complete search history.

(56) References Cited

U.S. PATENT DOCUMENTS

| 6,905,586 B2 | 6/2005 | Lee et al. |
| 2010/0331194 A1 | 12/2010 | Turner et al. |
| 2011/0236984 A1* | 9/2011 | Sun ...................... C12Q 1/6869 436/94 |

OTHER PUBLICATIONS

Johan Lagerqvist, Michael Zwolak, and Massimiliano Di Ventra, "Fast DNA Sequencing via Transverse Electronic Transport", Nano Letters, 2006 vol. 6, No. 4, pp. 779-782.
Prasongkit et al., Transverse Conductance of DNA Nucleotides in a Graphene Nanogap from First Principles, Nano Letters, May 11, 2011 (Epub Apr. 2011), vol. 11, No. 5, pp. 1941-1945.

(Continued)

*Primary Examiner* — Sally Merkling
(74) *Attorney, Agent, or Firm* — Miles & Stockbridge P.C.

(57) ABSTRACT

Provided is a device that, on the basis of a measurement result of a current that has a low value and a wide distribution, identifies the composition of biological molecules passing through a nanoparticle path. This biomolecule information analysis device obtains a current value by applying an electrical field to biomolecules passing through a gap between a first electrode and a second electrode, and identifies the structure of the biomolecules by integrating the current value and making a comparison with a reference value (see FIG. 1).

15 Claims, 42 Drawing Sheets

(56) References Cited

OTHER PUBLICATIONS

Postma, Henk W. CH., Rapid Sequencing of Individual DNA Molecules in Graphene Nanogaps, Nano Letters, 2010, vol. 10, No. 2, pp. 420-425.
Krems, et al. "Effect of Noise on DNA Sequencing via Transverse Electronic Transport", Biophysical Journal, 2009, vol. 97, No. 7, pp. 1990-1996.
Gierhart, et al. "Nanopore with Transverse Nanoelectrodes for Electrical Characterization and Sequencing of DNA", Sensors and Actuators, Science Direct El Sevier, 2008, vol. 132, No. 2, pp. 593-600.
Sigalov, et al. "Detection of DNA Sequences Using an Alternating Electric Field in a Nanopore Capacitor", Nano Letters, 2008, vol. 8, No. 1, pp. 56-63.
Schlecht, et al., "Detection of Rev peptides with impedance-sensors—Comparison of device-geometries", Biosensors & Bioelectronics, 2007, vol. 22, No. 9-10, pp. 2337-2340.
Yi et al., "Theoretical and experimental study towards a nanogap dielectric biosensor", Biosensors & Bioelectronics, 2005, vol. 20, No. 7, pp. 1320-1326.
Timp, et al. "Single Molecule Detection Using a Silicon Nanopore-Nanotransistor Integrated Circuit", AD report, 2006, pp. 1-14.

\* cited by examiner

| Nucleotide | SAO<0> | SAO<1> | SAO<2> | RO<0> | RO<1> |
|---|---|---|---|---|---|
| A | 1 | 1 | 1 | 1 | 0 |
| G | 0 | 1 | 1 | 1 | 1 |
| C | 0 | 0 | 1 | 0 | 1 |
| T | 0 | 0 | 0 | 0 | 0 |

| base | SAO0 | SAO1 | SAO2 |
|------|------|------|------|
| T | 1 | 1 | 1 |
| C | 1 | 1 | 0 |
| G | 1 | 0 | 0 |
| A | 0 | 0 | 0 |

FIG. 27
(a)
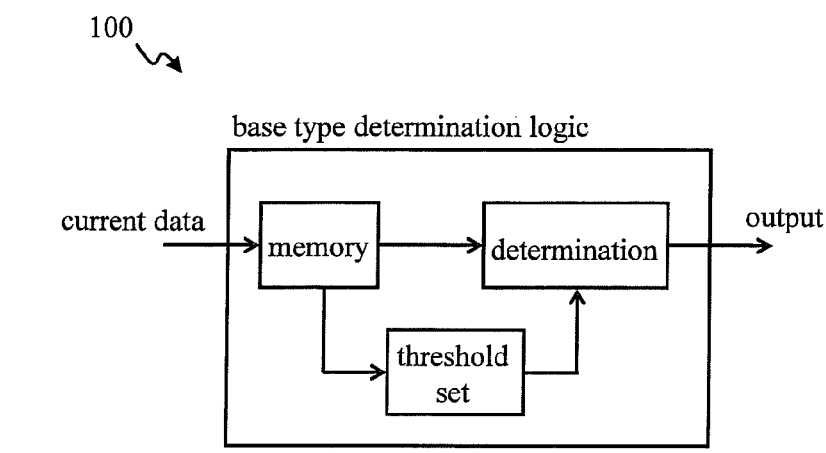
(b)
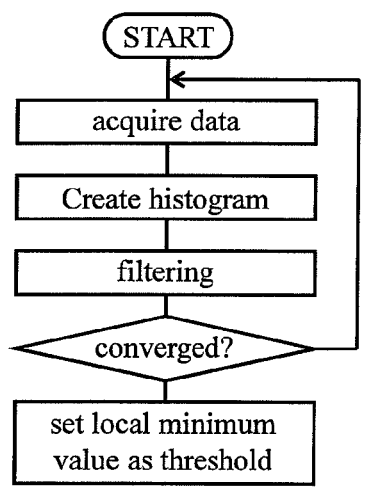

FIG. 28
(a)
without gain error
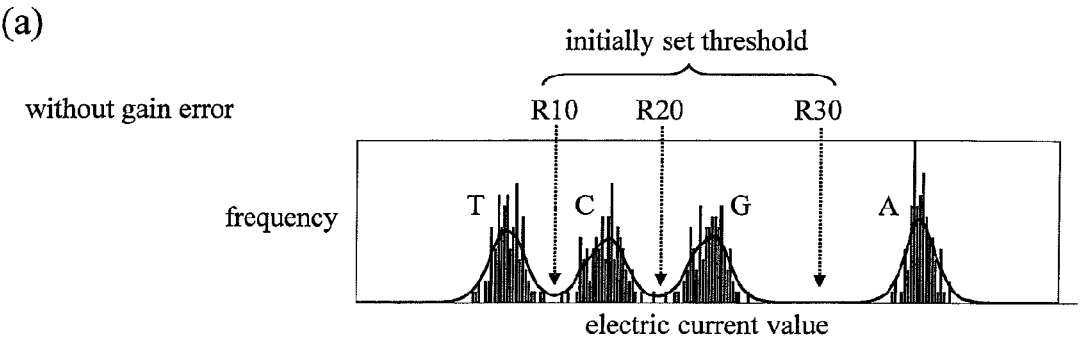
(b)
with gain error
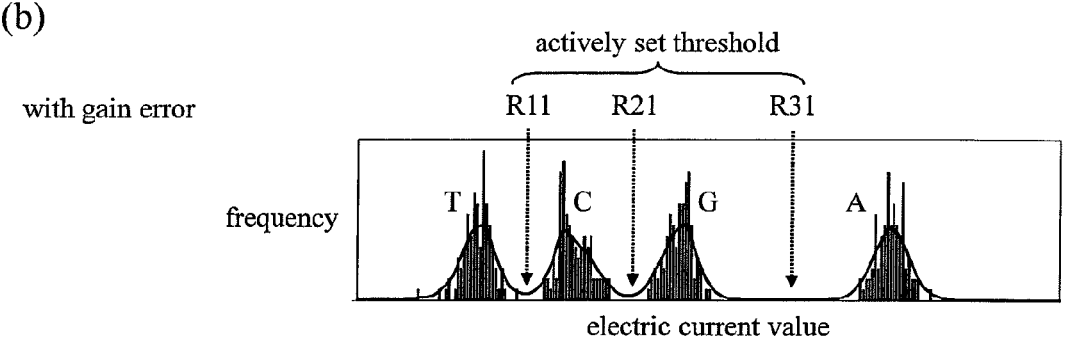

FIG. 31
(a)
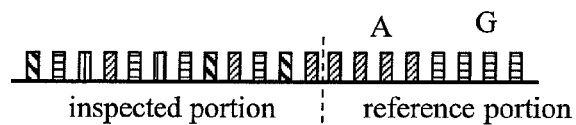
inspected portion | reference portion
(b)
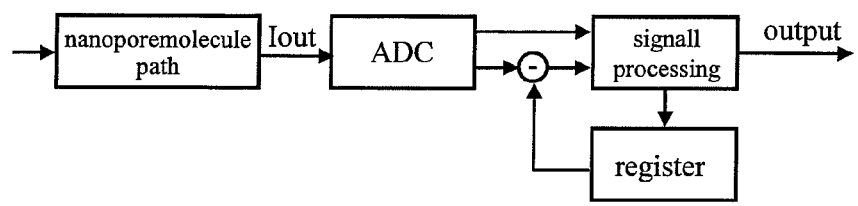
FIG. 32
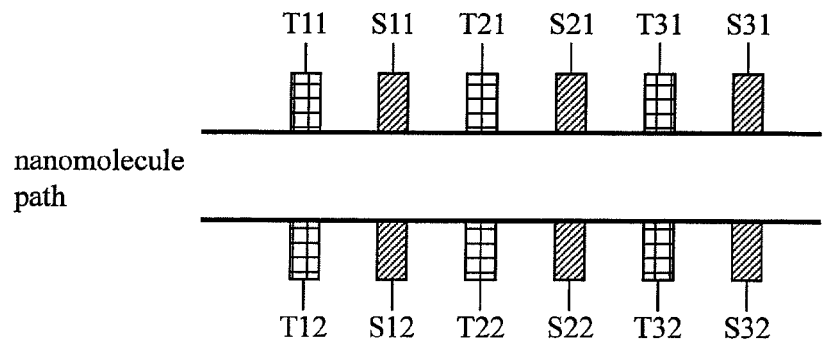

FIG. 33
(a) 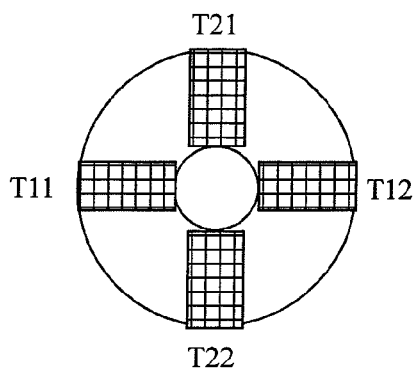
(b) 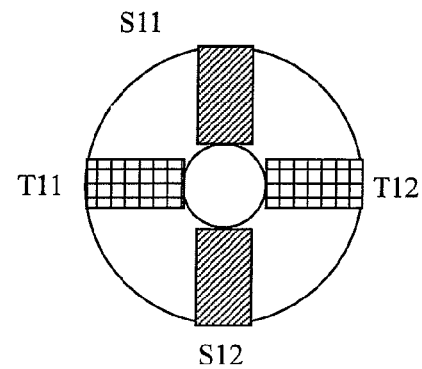
FIG. 34
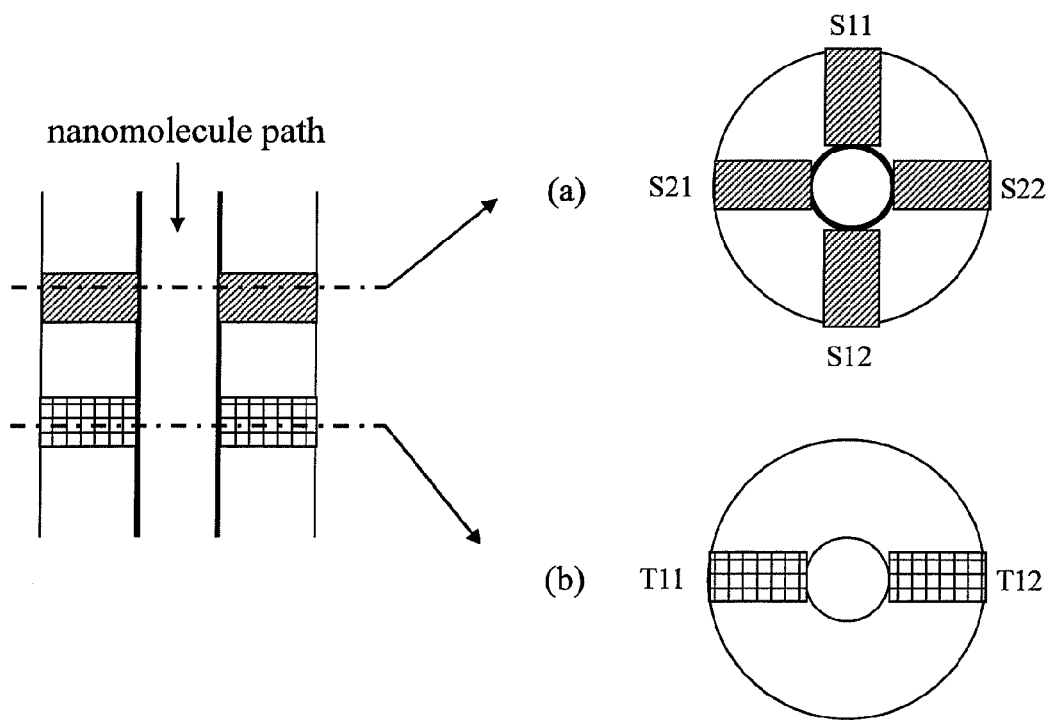

FIG. 43
(a)
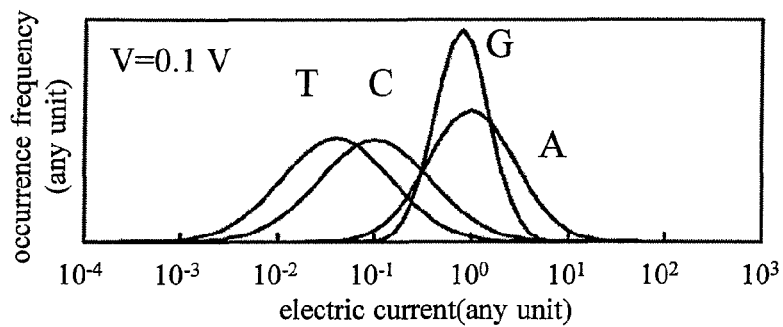
(b)
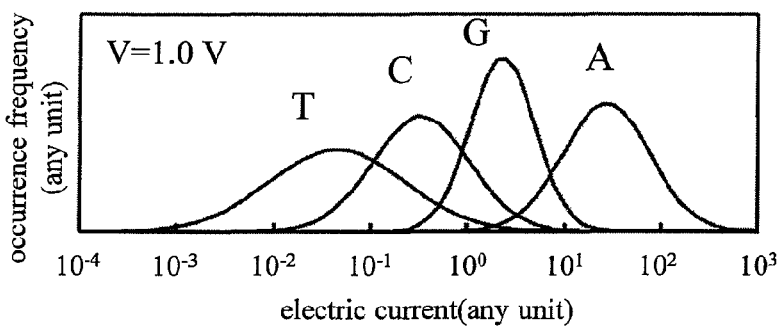
FIG. 44
(a)
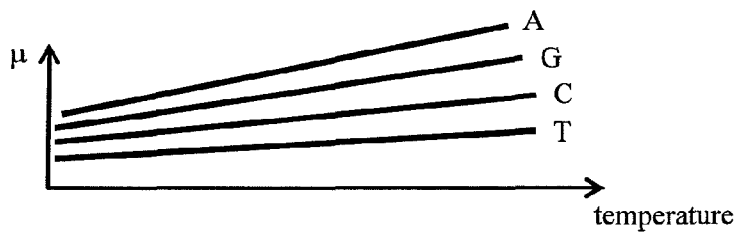
(b)
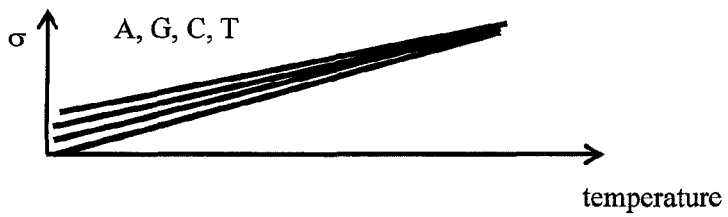

FIG. 48
(a)
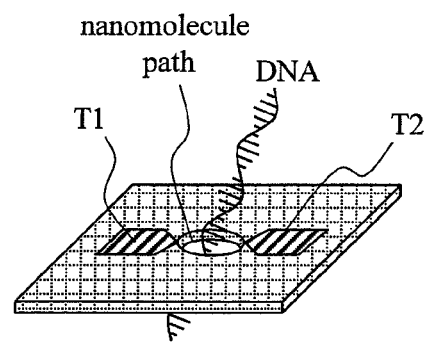
(b)
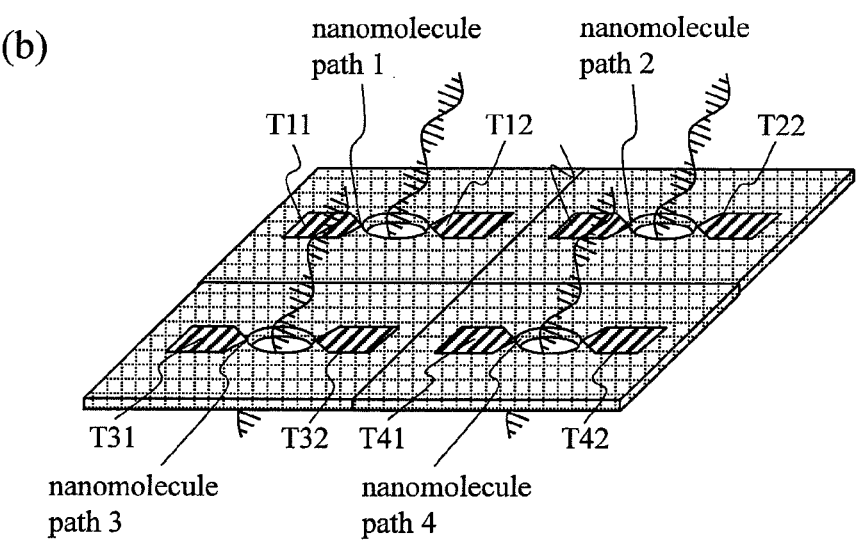

FIG. 51
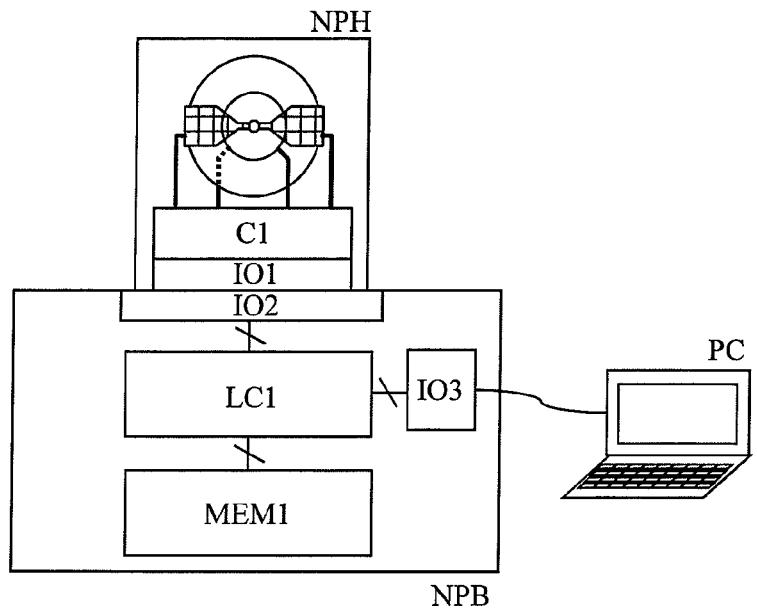
FIG. 52
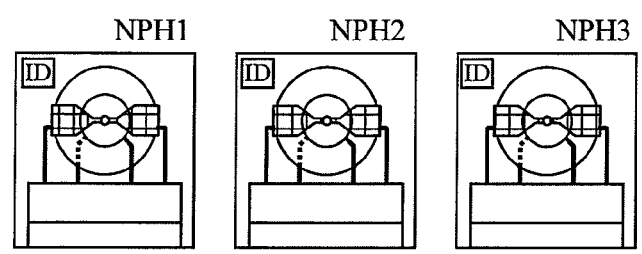
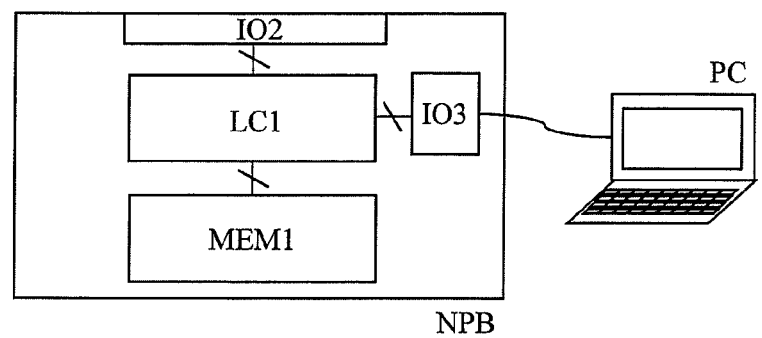

FIG. 57
(a)
through silicon via
(a-1)                    (a-2)
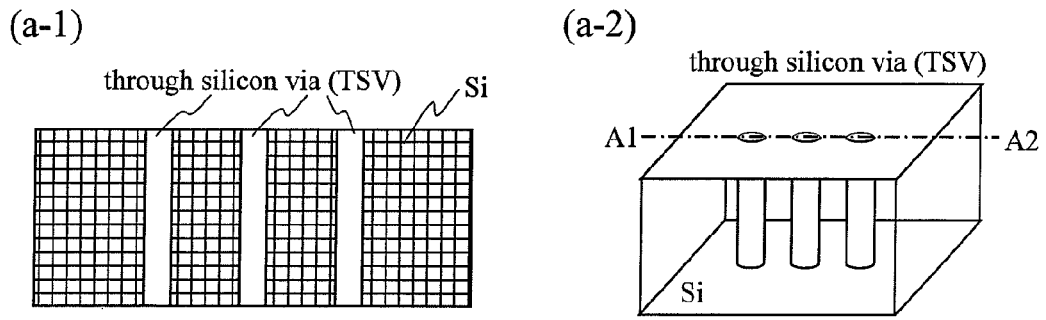
(b)
connection by
through silicon via
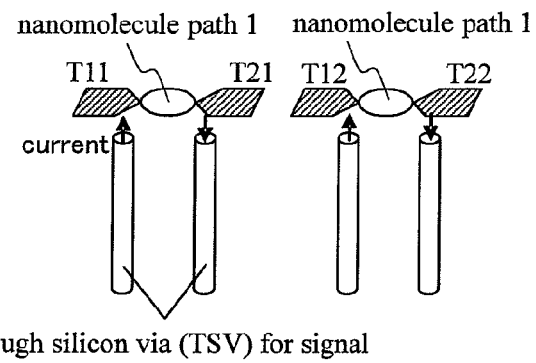
(c)
connection using
TSVs for shied and signal
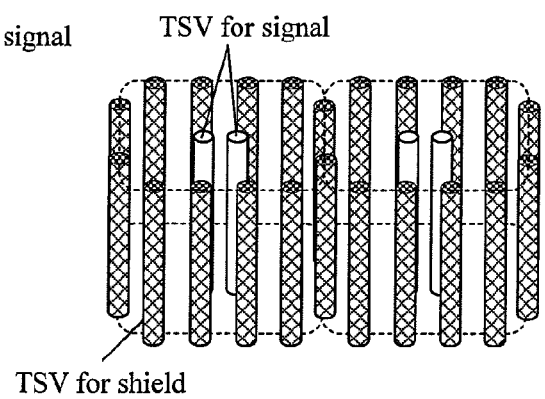

BIOMOLECULE INFORMATION ANALYSIS DEVICE

TECHNICAL FIELD

The present invention relates to an apparatus that acquires biomolecule information and analyses it.

BACKGROUND ART

With the development in semiconductor micromachining techniques, it has become possible to perform machining in nanometer (nm) scale. Utilizing such techniques, a technology for analyzing nano-scale biomolecules such as DNA (Deoxyribo Nucleic Acid) molecules carrying genetic information has been developed.

FIG. 58 is a diagram showing a structural example of DNA molecule. A DNA molecule is formed by four types of bases (adenine (A), thymine (T), guanine (G), cytosine (C)) coupled to a polynucleotide chain.

FIG. 59 is a diagram showing a helical structure of a DNA molecule. As shown in FIG. 59 (a), it is known that a DNA molecule has a double helix structure comprising two chains. A and T, G and C respectively form pairs and are coupled by hydrogen bonding in the bases of each chain. When the double helix structure is formed, these pairs of bases are aligned with a spacing of about 0.34 nm from the polynucleotide chain. When the two chains are uncoupled to be single chains, the bases are aligned with a spacing of about 0.7 nm.

Namely, semiconductor micromachining techniques reach the technical level of machining nanostructures as small as inner structures of DNA molecules, which is an example of biomolecules. Therefore, it is possible to investigate characteristics of biomolecules according to electrical or mechanical characteristics of semiconductors.

FIG. 59 (b) is a diagram showing a single chain extracted from FIG. 59 (a). FIG. 59 (c) is a schematic diagram showing the single chain in which the helical structure is unbound. In this description, a single chain is shown as FIG. 59 (d) (e) (f) in some cases.

Because of aged society, there is a social need for detailed health managements or health cares on the basis of personal genetic information. Thus a technology has been developed for cost-effectively and rapidly analyzing personal genetic information using semiconductor micromachining techniques and semiconductor techniques. Since effects of medicines or management processes of health conditions are dependent on personal genetic information, the development is intended to promote medical care according to personal characteristics by analyzing personal genetic information.

FIGS. 60 and 61 are diagrams showing configuration examples of a DNA analysis apparatus. This apparatus: leads, for example, a single chain DNA or RNA (Ribo Nucleic Acid) to a small gap or a through hole formed by semiconductor micromachining technique; measures electric currents flowing through an electrode attached to the gap or the through hole; and analyzes structures or characteristics of DNA or RNA using the measurement results thereof. Hereinafter, the small gap or the through hole through which DNA or RNA passes is referred to as nanomolecule path. Other than DNA or RNA, general bio polymers such as enzyme or certain types of bacteria could be targets of the apparatus.

FIG. 60 is a diagram showing a configuration example of a DNA analysis apparatus in which DNAs pass via through holes (nanopores) formed by semiconductor micromachining technique. FIG. 60 (a) is a plain view, FIG. 60 (b) is a A-A' sectional view of FIG. 60 (a), and FIG. 60 (c) is a B-B' sectional view of FIG. 60 (a).

In FIG. 60 (a), the nanomolecule path is formed as a hole in which a part of Si plane is, for example, penetrated to the back surface. If the nanomolecule path is of circular shape, the diameter of the hole is about 1.5 nm to 3 nm. As shown in FIG. 60 (b), electrodes T1 and T2 are sandwiching the nanomolecule path and are sandwiched by thin film S1 and S2. As shown in FIG. 60 (c), portions other than the electrodes T1 and T2 are filled with a thin film S0. The S0, S1, and S2 are, for example, formed by silicon or silicon oxide or silicon nitride. The electrodes T1 and T2 are formed by titanium nitride or gold.

FIG. 61 is a diagram showing a configuration example of a DNA analysis apparatus in which DNAs pass through a small gap (nanogap) formed by semiconductor micromachining technique between the electrodes T1 and T2. FIG. 61 (a) is a plain view and FIG. 61 (b) is a A-A' sectional view of FIG. 61 (a). As shown in FIG. 61 (a), the electrodes T1 and T2 sandwiched by the thin film S1 and S2 form a nanomolecule path as the small gap on the thin film S0 which works as the lower surface of the path.

Patent Literature 1 listed below discloses an apparatus in which a microgap is provided between two electrodes having a structure similar to FIG. 61, and the apparatus reads tunnel electrical currents that flow when DNAs pass through the gap. In Patent Literature 1, two electrodes are set up in two directions perpendicular to two electrodes facing to each other so that bases of DNA pass through at a desired speed, and voltages are applied to the electrodes to generate electric fields. The electric field may control the speed at which the bases of DNA pass through the gap.

Patent Literature 2 listed below discloses an apparatus in which DNAs pass through a microhole having a structure similar to FIG. 60. In Patent Literature 2, the microhole itself does not have electrodes and electrodes are set up above and below the microhole. Electric currents flowing through the electrodes are different depending on types of four bases included in DNA. Therefore, it is possible to identify types of bases passing through the microhole by comparing the electric current with table data prepared in advance.

FIG. 62 is a diagram showing an example of electric current flowing to two electrodes having a microgap or to two electrodes facing toward an opening direction of a microhole. FIG. 62 schematically shows FIG. 3 of Non Patent Literature 1 listed below. The vertical axis indicates amount of electric current flowing between the two electrodes and the vertical axis indicates occurrence frequency of the electric current for each measurement.

As shown in FIG. 62, the electric current flowing through the two electrodes distributes with respect to the measurement. In addition, large portions of the four bases overlap with each other. All distributions of the four bases spread across more than 5 digits. The distribution is caused because of the positional relationship between the base molecules and the electrodes, the relationship between the direction of the base molecules and the electrodes, the movement of the base molecules with respect to the nucleotide chain, thermal vibration of the base molecules, the orientation or vibration of the DNA molecules caused by the electric field of the electrode, and the like. Non Patent Literature 1 describes that such distributions are caused. However, it does not specifically disclose how each of bases is identified according to distributions which include overlapping portions.

CITATION LIST

Patent Literature

Patent Literature 1: U.S. Pat. No. 6,905,586
Patent Literature 2: US Patent Publication 2010/0331194

Non Patent Literature

Non Patent Literature 1: Johan Lagerqvist, Michael Zwolak, and Massimiliano Di Ventra, "Fast DNA Sequencing via Transverse Electronic Transport", NANO LETTERS 2006 Vol. 6, No. 4, pp. 779-782

SUMMARY OF INVENTION

Technical Problem

As mentioned above, the electric current flowing through the two electrodes for analyzing biomolecule structures is different in the distribution peak and the shape for each of the bases. The distribution spreads across several digits, and the absolute value of the electric current is in nano ampere or pico ampere order. Patent Literatures 1-2 and Non Patent Literature 1 do not disclose measuring methods considering these conditions.

The present invention has been made to solve the problem stated above, and it is an objective of the present invention to provide an apparatus that identifies nanomolecule structures passing through nanomolecule paths according to measurement results of electric currents having a wide distribution with small values as described above.

Solution to Problem

The biomolecule information analysis apparatus according to the present invention applies an electric field to a biomolecule passing through a gap between first and second electrodes to acquire an electric current value, and identifies a biomolecule structure by integrating the electric current value and comparing the integrated value with a reference value.

Advantageous Effects of Invention

With a biomolecule information analysis apparatus according to the present invention, it is possible to accurately identify biomolecule structures.

BRIEF DESCRIPTION OF DRAWINGS

FIG. 27 is a diagram showing a configuration of a base type determination logic performed by the logic circuit LOGIC in the embodiment 8.

FIG. 28 is a diagram showing that the electric current distribution changes due to the gain error (gain variation) of the amplifier.

FIG. 31 is a diagram showing another configuration example of the bases used as the reference input.

FIG. 32 is a diagram showing a configuration of the nanomolecule path in the embodiment 10.

FIG. 33 is a diagram showing a configuration example of the nanomolecule path in an embodiment 11.

FIG. 34 is a diagram showing a configuration example in which multiple electrodes are set up in the thickness direction of the nanomolecule path formed as a through hole.

FIG. 43 is a diagram showing a distribution of base electric currents in cases where the bias voltages are 0.1 V and 1 V respectively.

FIG. 44 is a diagram showing that the distribution of the base electric current varies depending on temperature.

FIG. 48 is a diagram in which the nanomolecule path in FIG. 47 is extracted.

FIG. 51 is a diagram showing a configuration of peripheral devices around the device NPH.

FIG. 52 is a diagram showing a configuration example in which the device NPH as the head unit may be removable from the device NPB.

FIG. 57 is a diagram showing a configuration of a through silicon via.

DESCRIPTION OF EMBODIMENTS

Embodiment 1

Figure 1:
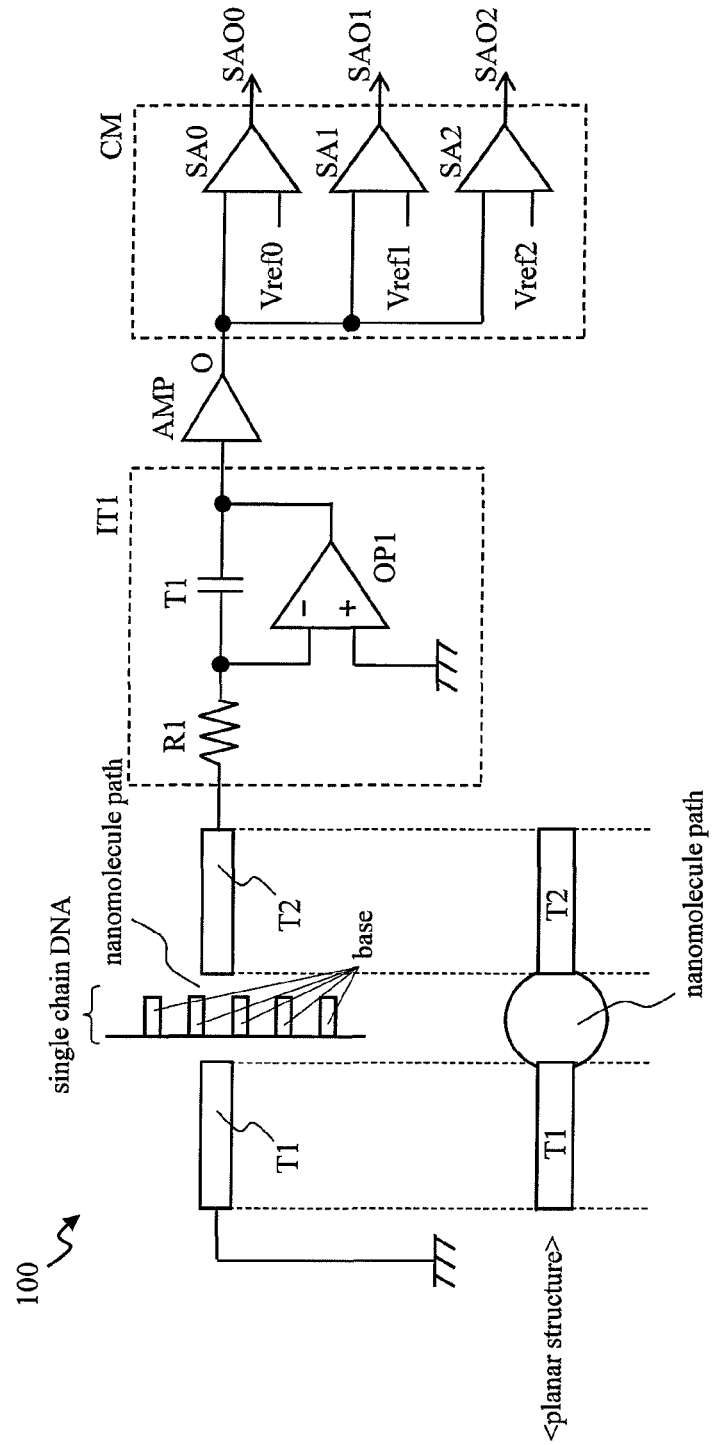
FIG. 1 is a configuration diagram of a biomolecule information analysis apparatus 100 according to an embodiment 1.

FIG. 1 is a configuration diagram of a biomolecule information analysis apparatus 100 according to an embodiment 1 of the present invention. T1 and T2 are electrodes. The gap between the electrodes T1 and T2 forms a part of a nanomolecule path (nanopore). A single chain DNA passes through the nanomolecule path. The single chain DNA includes four types of bases. The sequence of the bases carries genetic information. The electrode T1 is grounded. The electrode T2 is connected to an integration circuit IT1. The electric current between the electrodes T1 and T2 is different depending on the type of the base of the DNA between the electrodes T1 and T2.

The integration circuit IT1 includes a resistor R1, a capacitor T1, and an operational amplifier OP1. The integration circuit IT1 integrates the electric current between the electrodes T1 and T2, and outputs the result thereof to an amplifier AMP. The output from the amplifier is O. The output O is inputted into a comparator CM.

The comparator CM includes sense amplifiers SA0, SA1, and SA2. The outputs from these sense amplifiers are SAO0, SAO1, and SAO2 respectively. Each sense amplifier compares each of reference voltages Vref0, Vref1, and Vref2 respectively with the output O from the AMP, thereby acquiring different voltages for each of four bases. The integration time required for determining the type of one base is about 10 μs.

Figure 2:
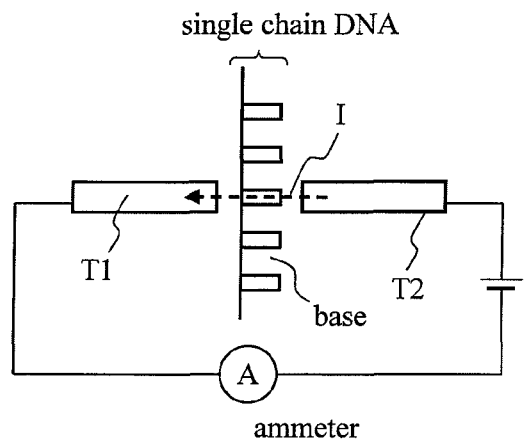
FIG. 2 is a diagram showing a detailed configuration around the nanomolecule path included in the biomolecule information analysis apparatus 100.

FIG. 2 is a diagram showing a detailed configuration around the nanomolecule path included in the biomolecule information analysis apparatus 100. The electrodes T1 and T2 are connected to a power source and are further connected to an ammeter for measuring electric currents. The electric current flowing through the single chain DNA is I. As described with FIG. 62, this electric current is distributed.

The distribution described with FIG. 62 will be supplemented below. The horizontal axis of FIG. 62 indicates the amount of electric current I flowing between the two electrodes and is shown with logarithmic axis. The vertical axis indicates occurrence frequency of the electric current for each of measurement and is shown with linear axis. A, T, G, and C are types of bases that have passed through between the electrodes. For example, a measurement is performed by applying an electric voltage 1V between the electrodes T1 and T2 for duration of 1 ns to cause an electric current to flow. This measurement is repeated for multiple times to acquire electric current values indicated in the horizontal axis and the occurrence frequency of the electric current value is indicated in the vertical axis.

Figure 62:
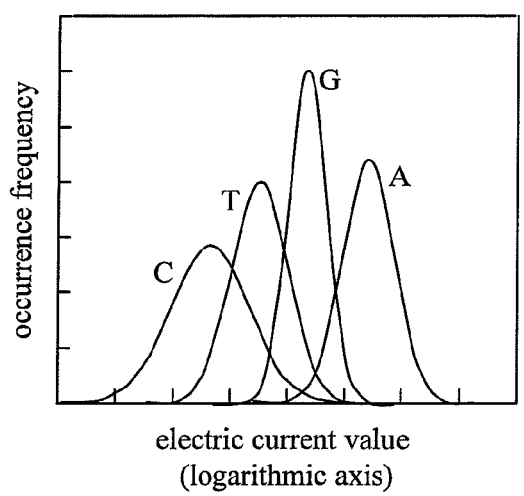
FIG. 62 is a diagram showing an example of electric current flowing to two electrodes having a microgap or to two electrodes facing toward an opening direction of a microhole.

As can be seen from FIG. 62, each of the four bases has different distributions. The dispersion σ of the distribution and the electric current value μ corresponding to the maximum frequency are different for each of the four bases. In addition, the trails of the distribution are not separated and the distributions corresponding to each base are overlapping with each other. Therefore, for example, when C or T passes through the electrodes, they exhibit the same electric current value in some cases, which may inhibit from precisely identifying the base.

In the embodiment 1, in order to address the above-described problem, the integration circuit IT1 that integrates the electric current value flowing through the electrode T2 is provided. The integration circuit IT1 is a circuit that accumulates electric charges corresponding to a product of an electric current flowing at one measurement and measurement time thereof. The accumulated result of the integration circuit IT1 can be read out in the form of changes in voltage. Alternatively, the accumulated result can be read out in the form of changes in voltage by causing electric currents to flow continuously and integrating the electric current value by the measurement time to accumulate electric charges.

Figure 3:
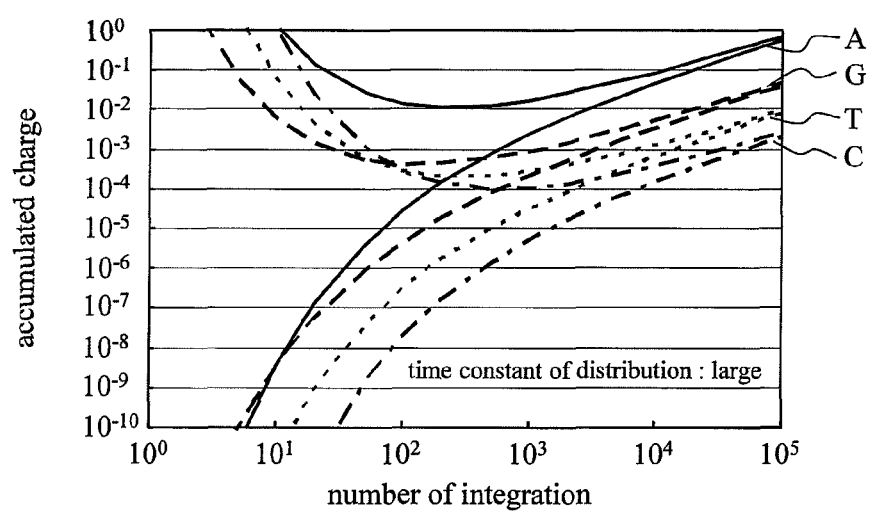
FIG. 3 is a diagram showing a relationship between electric charge accumulated by the integration circuit IT1 and number of integration.

FIG. 3 is a diagram showing a relationship between electric charge accumulated by the integration circuit IT1 and number of integration. In one measurement, a product of an electric current value and measurement time thereof is calculated. The number of measurement, namely the number of integration is plotted along the horizontal axis. The accumulated electric charge for each number of integration is plotted along the vertical axis. If the electric current flows continuously, the horizontal axis corresponds to the integration time.

Since the electric current flowing through the electrode has a distribution, an electric current value in one measurement stochastically varies in the distribution. Therefore, assuming the base A as an example, the accumulated electric charge takes values between the maximum and the minimum electric currents in the distribution if the number of integration is small. As the number of integration becomes large, the accumulated electric charge converges into almost one single line. This is because the electric current values that are stochastically present in the distribution appear evenly as the number of integration becomes large. This applies to other bases.

The present inventors have found that the converged value is different depending on the bases and that the converged values can be clearly distinguished from each other. Therefore, even if the electric currents measured for each base has a distribution and the trails overlap with each other, the bases can be identified by distinguishing the converged values. Namely, since the integration circuit IT1 exhibits electric voltage values corresponding to each of four bases depending on the accumulated electric charge, the comparator CM may identify the base that corresponds to the electric voltage value using three reference voltages.

Note that the speed at which the accumulated electric charge converges with respect to the number of integration depends on the time constant of the event causing the electric current distribution. This is because the event contributing to the measured electric current is different depending on temperature, solvent, and applied voltage.

Figure 4:
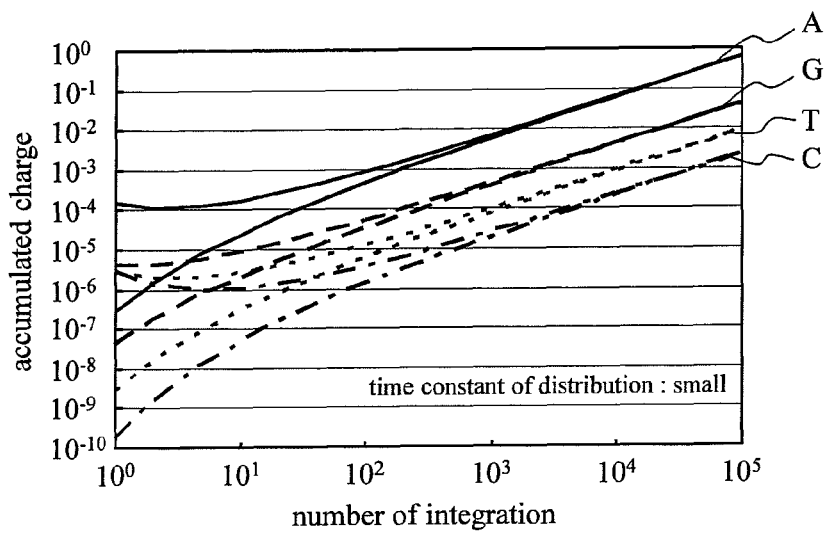
FIG. 4 is a diagram showing a relationship between the electric charge accumulated by the integration circuit IT1 and the number of integration in a case where the time constant causing the electric current distribution is smaller than that of FIG. 3.

FIG. 4 is a diagram showing a relationship between the electric charge accumulated by the integration circuit IT1 and the number of integration in a case where the time constant causing the electric current distribution is smaller than that of FIG. 3. As obvious from FIG. 4, comparing the numbers of integration required for the accumulated electric charge to converge, A is the smallest followed by G, T, and C in this order. In this case, if the accumulated electric charge is read out by converting it to electric voltages, A, G, T, and C respectively reaches the reference electric voltage (VREF) in this order. Using this characteristic, the bases can be distinguished using the number of integration or the integration time by which the electric voltage reaches the reference electric voltage VREF.

Embodiment 1: Summary

As discussed thus far, the biomolecule information analysis apparatus 100 according to the embodiment 1 integrates the electric current flowing through the electrode T2, and identifies biomolecule structures according to the number of integration or the integration time by which the electric voltage indicating the electric charge accumulated by the integration circuit IT1 reaches the reference electric voltage VREF. This enables identifying biomolecule structures in the nanomolecule path even if the measured electric current value is small, the distribution spreads widely, and the distribution overlaps.

In addition, with the biomolecule information analysis apparatus 100 according to the embodiment 1, it is possible to rapidly and precisely analyze information (base arrangement in case of DNA) of biomolecules such as DNA in which the data acquired by measurement distributes. This enables promoting personal medical cares in which health management or health care are performed on the basis of personal biological information or genetic information.

Embodiment 2

In FIG. 4 of the embodiment 1, it is described that the bases can be distinguished by the number of integration or the integration time by which the electric voltage corresponding to the accumulated electric charge of the integration circuit IT1 reaches the reference electric voltage VREF. In an embodiment 2 of the present invention, a configuration example will be described in which the same configuration is achieved for the integration time.

Figure 5:
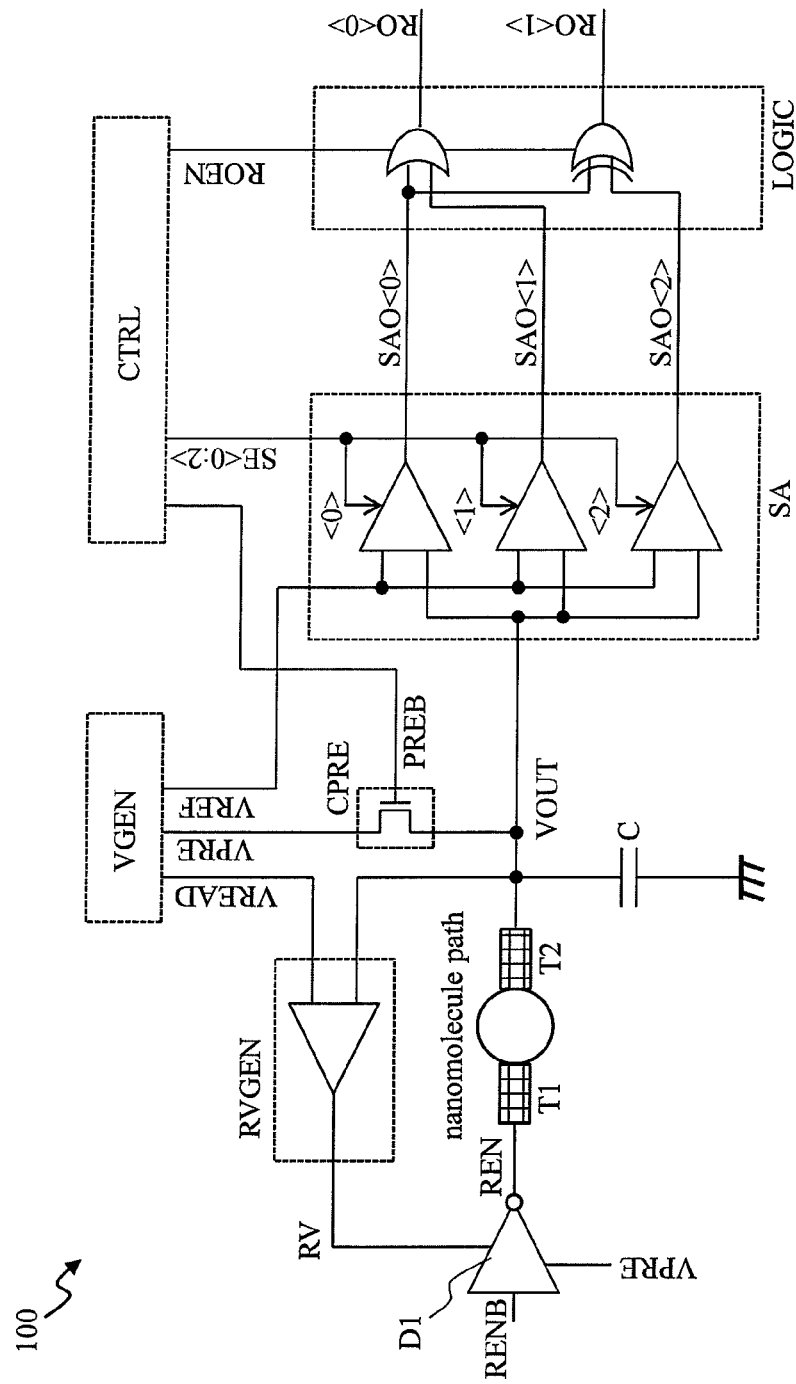
FIG. 5 is a diagram showing a configuration of a biomolecule information analysis apparatus 100 according to the embodiment 2.

FIG. 5 is a diagram showing a configuration of a biomolecule information analysis apparatus 100 according to the embodiment 2. A driver D1 is a circuit that drives the electrodes T1 and T2. The input of the driver D1 is RENB and the output is REN. The output REN is connected to the electrode T1.

An electric power source circuit VGEN outputs a precharge electric voltage VPRE, a bias reference electric voltage VREAD, and the reference electric voltage VREF. The electrode T2 outputs an output VOUT. A capacitor C, a precharge circuit CPRE, and a sense amplifier SA are connected to the output terminal of the electrode T2. The sense amplifier SA is a circuit that determines the type of bases according to the electric voltage value of the output VOUT. The precharge electric voltage VPRE and its control signal VPREB are inputted to the precharge circuit CPRE. The output VOUT is also inputted to a bias electric voltage application circuit RVGEN. The bias electric voltage application circuit RVGEN outputs to the driver circuit D1, according to the output VOUT and the bias reference electric voltage VREAD, a bias electric voltage RV at the time of flowing electric current through bases.

The sense amplifier SA compares the reference electric voltage VREF with the output VOUT. The sense amplifier SA includes three amplifiers. The reference electric value VREF and the output VOUT are inputted to each of the amplifiers. The outputs of each amplifier are SAO<0>, SAO<1>, and SAO<2>. The control signals for each amplifier are SE<0:2>. The control signal SE defines the timing at which the output VOUT is compared with the reference electric voltage VREF. Details will be described with reference to FIG. 6 later.

The outputs from the three amplifiers are outputted as digital outputs to a logic circuit LOGIC. The logic circuit LOGIC performs a logical operation described with FIG. 7 later to output outputs RO<0> and RO<1>. Since two bits information is required to determine four bases, the outputs RO<0> and RO<1> are provided. A control signal ROEN is a control signal for the logic circuit LOGIC.

Figures 6, 7:
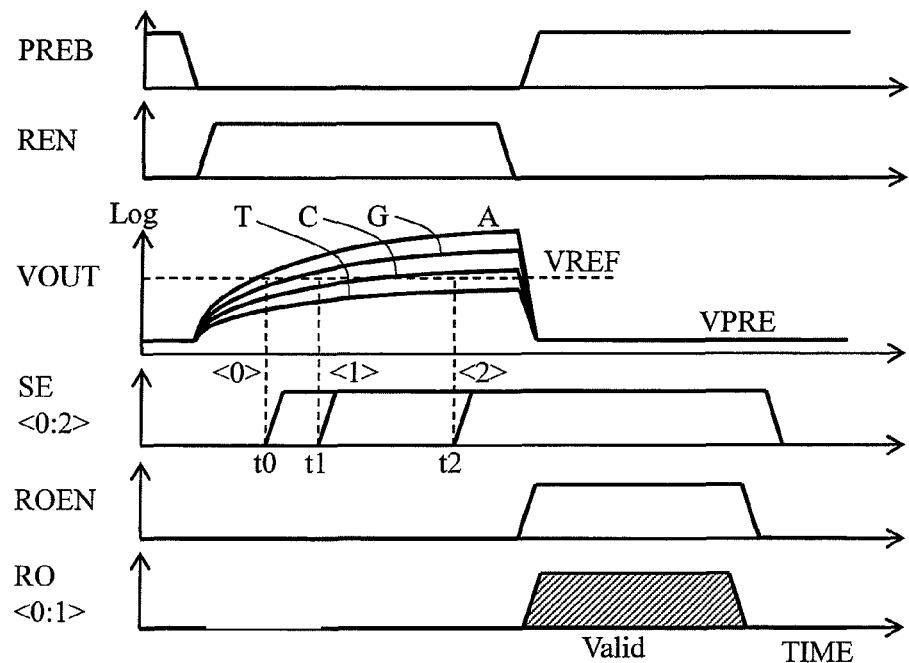
FIG. 6 is a diagram showing an operation of the biomolecule information analysis apparatus 100 according to the embodiment 2.
FIG. 7 is a correspondence table showing how the outputs SAO<0> to SAO<2> of the sense amplifier SA and the outputs RO<0> to RO<1> of the logic circuit LOGIC describe the typed of bases.

FIG. 6 is a diagram showing an operation of the biomolecule information analysis apparatus 100 according to the embodiment 2. After precharge of the output VOUT is completed and the precharge control signal PREB becomes low-level, the driver D1 operates to output the output REN. Electric currents corresponding to the types of bases flow through the electrode T2 to change the output VOUT. This electric current has a distribution, thus the change in electric voltage value corresponding to the accumulated electric charge converged by time integration differs depending on the type of bases. As described with reference to FIG. 4 of the embodiment 1, the type of bases can be identified by the difference of time by which the electric voltage value reaches the reference electric voltage VREF.

As shown in the waveform of the output VOUT, A reaches the reference electric voltage VREF at first and T reaches at last. This time difference can be used to control, by the control signals SE<0:2>, the timing for comparing with the reference electric voltage VFRE. Each of the bases is compared with VREF at time t0, t1, and t2 respectively. For example, at the time t0, only the electric voltage value of A has reached the reference electric voltage VREF. At the time t2, A, G, and C have reached. This time difference enables identifying each of the bases. The identification result appears in the outputs SA<0>, SAO<1>, and SAO<2> of the sense simplifier SA.

After the sense amplifier SA outputs the outputs SAO<0> to SAO<2>, the control signal REON initiates the logic circuit LOGIC to perform the logical operation. The identification result appears in the outputs RO<0> and RO<1>.

FIG. 7 is a correspondence table showing how the outputs SAO<0> to SAO<2> of the sense amplifier SA and the outputs RO<0> to RO<1> of the logic circuit LOGIC describe the typed of bases. For example, in the case of A, the outputs SAO<0> to SAO<2> are all "1", the output RO<0> is "1", and the output RO<1> is "0" when the logic circuit LOGIC is initiated. When the outputs RO<0> to RO<1> are acquired, the type of base is determined as A. The time duration required for the integration is about 10 μs as in the embodiment 1.

Embodiment 2: Summary

As discussed thus far, with the biomolecule information analysis apparatus 100 according to the embodiment 2, the same effect as that of the embodiment 1 can be obtained. In addition, in contrast to the embodiment 1, only one reference electric voltage VREF is necessary.

Embodiment 3

Figure 8:
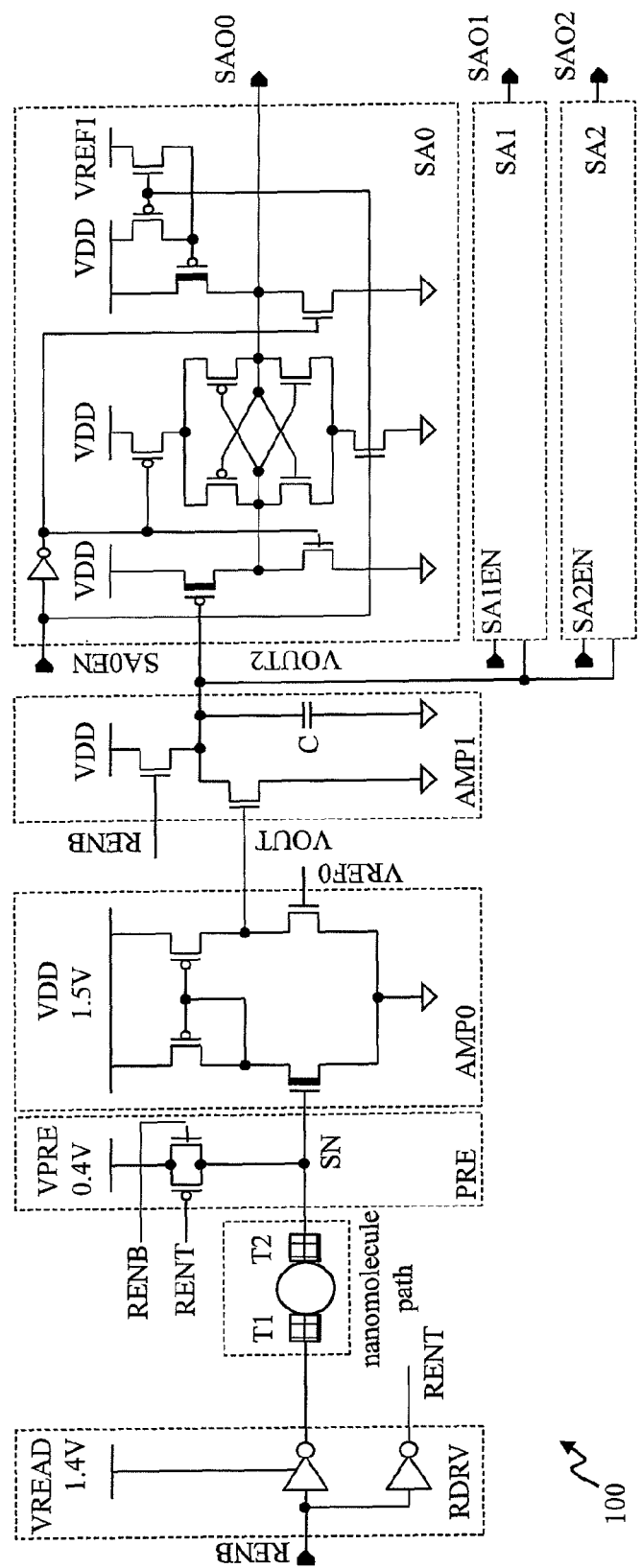
FIG. 8 is a configuration diagram of a biomolecule information analysis apparatus 100 according to an embodiment 3.

FIG. 8 is a configuration diagram of a biomolecule information analysis apparatus 100 according to an embodiment 3 of the present invention. The biomolecule information analysis apparatus 100 according to the embodiment 3 includes, in addition to the configuration described in the embodiment 2, an amplifier in the integration circuit.

A driver RDRV drives the electrodes T1 and T2. PRE is a precharge circuit. Amplifiers AMP0 and AMP1 work as integration circuits including amplifiers. SA0, SA1, and SA2 are sense amplifiers that determine types of bases according to the output from the integration circuit and the reference electric voltage VREF. The logic circuit LOGIC described in the embodiment 2 is omitted in the figure.

The electrodes T1 and T2 have a nanomolecule path formed with microgaps or microholes. The driver RDRV applies an electric voltage to the electrodes T1 and T2 in accordance with the bias reference electric voltage VREAD. The control signal RENB controls the driver RDRV. The value of the bias reference electric voltage VREAD is, for example, 1.4 V.

The precharge circuit PRE provides a terminal SN connected to the electrode T2 with a precharge electric voltage VPRE (0.4 V, for example). The control signals RENB and RENT control the precharge circuit PRE.

The amplifier AMP0 receives an output from the terminal SN, and amplifies the output using the reference electric voltage VREF0. The amplifier AMP0 has two characteristics. The first characteristic is that a power source electric voltage VDD (1.5 V, for example) and the electric voltage VPRE that drives or precharges the nanomolecule path can be independent from each other. This enables selecting and designing the electric voltage optimum for circuit operations of the biomolecule information analysis apparatus 100 and the electric voltage optimum for the nanomolecule path independently from each other. The second characteristic is that a MOS transistor for receiving the output from the terminal SN can be selected from those with low threshold electric voltage, thereby enabling high sensitivity.

As an example of the MOS transistor included in the amplifier AMP0, a transistor with thick gate oxide film may be selected. This is because it is desirable to reduce leak electric currents in order to detect very small electric currents flowing through bases. Recent micro MOS transistors use thin oxide films in order to improve performances. However, it causes large leak electric currents to flow through the gate. In some cases of MOS transistors for high performance processors, a leak electric current value with the same order as that of electric currents to be detected may flow through the gate. In the embodiment 3, it is possible to employ MOS transistors with thick gate oxide film to reduce leak electric currents. Thus it is not necessary to use MOS transistors with high performance, which is beneficial in terms of costs or the like.

The output VOUT from the amplifier AMP0 is inputted into the gate of the next stage amplifier AMP1. The drain output from the amplifier AMP1 is connected to a MOS transistor that is driven by an integration capacitor C and the control signal RENB and that precharges the capacitor C at the electric voltage VDD. The integrated output VOUT2 is inputted into the sense amplifiers SA0, SA1, and SA2.

The control signals SA0EN, SA1EN, and SA2EN initiate sense amplifiers SA0, SA1, SA2 respectively. The sense amplifiers are flip-flop type sense amplifiers. The sense amplifiers control the timings of the control signals SA0EN to SA2EN using a reference electric voltage generation circuit VREF1 as in the embodiment 2, and compare the output VOUT2 with the output from the reference electric voltage generation circuit VREF1 to output the comparison result as SAO0, SAO1, and SA2.

Figures 9, 10:
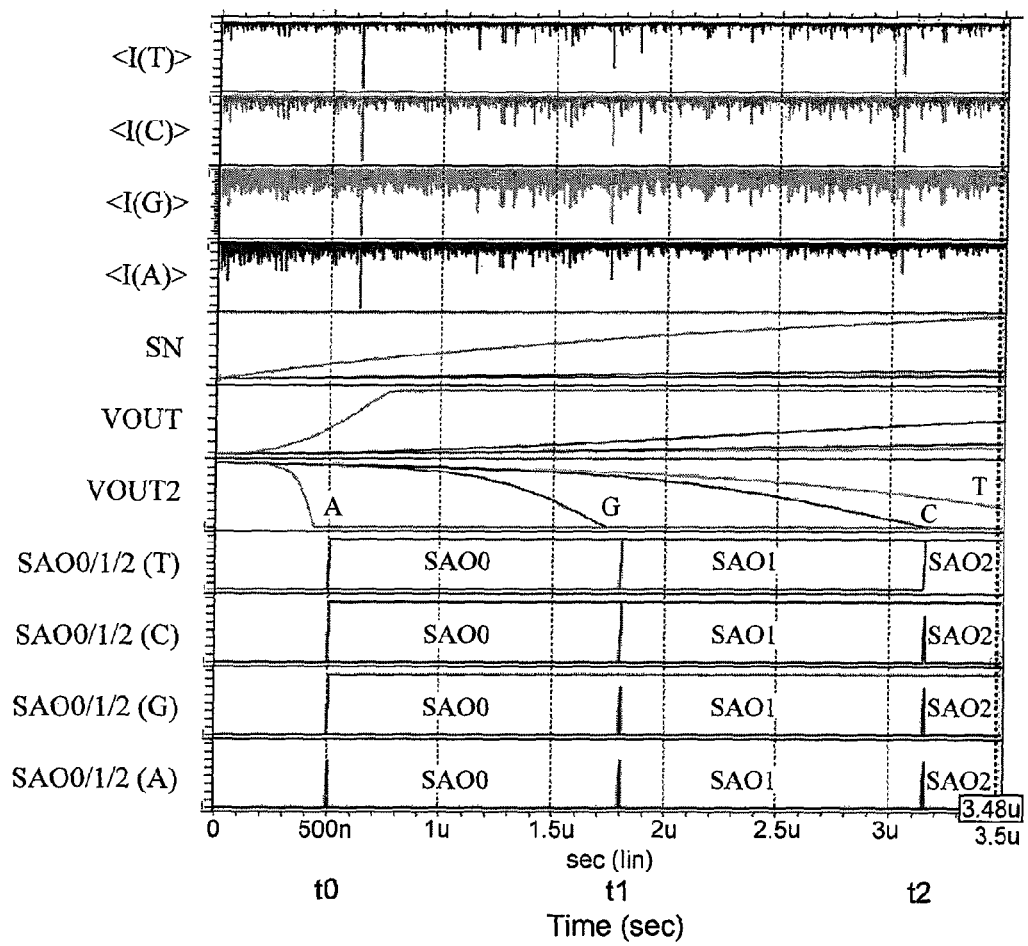
FIG. 9 is a diagram showing a circuit simulation of an operation of the biomolecule information analysis apparatus 100 according to the embodiment 3 using the electric current distribution as in FIG. 62.
FIG. 10 is a correspondence table between the values of the outputs SAO0 to SAO2 and the types of bases.

FIG. 9 is a diagram showing a circuit simulation of an operation of the biomolecule information analysis apparatus 100 according to the embodiment 3 using the electric current distribution as in FIG. 62. The electric current waveform of T is shown as <I(T)>, the electric current waveform of C is shown as <I(C)>, the electric current waveform of G is shown as <I(G)>, and the electric current waveform of A is shown as <I(A)>. The figure shows the change in electric voltage of the terminal SN connected to the electrode T2 and the change in electric voltage of the output VOUT from the amplifier AMP0, for the case of A respectively. Although not shown in the figure, the change in electric voltage of the terminal SN and the change in electric voltage of the output VOUT can be acquired for the cases of T, G, and A in accordance with each of waveforms.

The waveforms of four bases are overlapped for the output VOUT2. Along with the time axis, the waveform corresponding to A changes at first, followed by G, C, and T. At the times t0, t1, and t2, the outputs SAO0, SA1, and SAO2 are outputted respectively.

FIG. 10 is a correspondence table between the values of the outputs SAO0 to SAO2 and the types of bases. As shown in FIG. 10, the types of bases uniquely correspond to the outputs.

Embodiment 3: Summary

As discussed thus far, the embodiment 3 describes a specific example of the circuit configuration described in the embodiment 2. With the embodiment 3, it is possible to achieve the same effects as those of the embodiments 1 and 2. In addition, it is possible to achieve the above-mentioned effect regarding the amplifier AMP0.

Embodiment 4

In an embodiment 4 of the present invention, a configuration example will be described in which the types of bases are more rapidly and precisely identified utilizing that the bases constructing DNA chains are coupled as pairs in which two types of bases are included in one pair.

When a DNA comprises a double helix with two chains, it is known that A and T, G and C are coupled by hydrogen bonding forming pairs respectively. Utilizing it, it is possible to identify the bases more rapidly than the methods described in the embodiments 1 to 3. Namely, if a base in a pair can be identified, another base in the same pair can also be identified. Therefore, when unbinding a double helix to analyze two chains, it is sufficient to analyze two bases which are easier to analyze. The easiness of analysis corresponds to selecting two types of bases with larger electric currents, for example. This method can be applied when identifying pairs of other biomolecules. It can also be applied to use in spectroscopy or to multiplication of bases.

Figure 11:
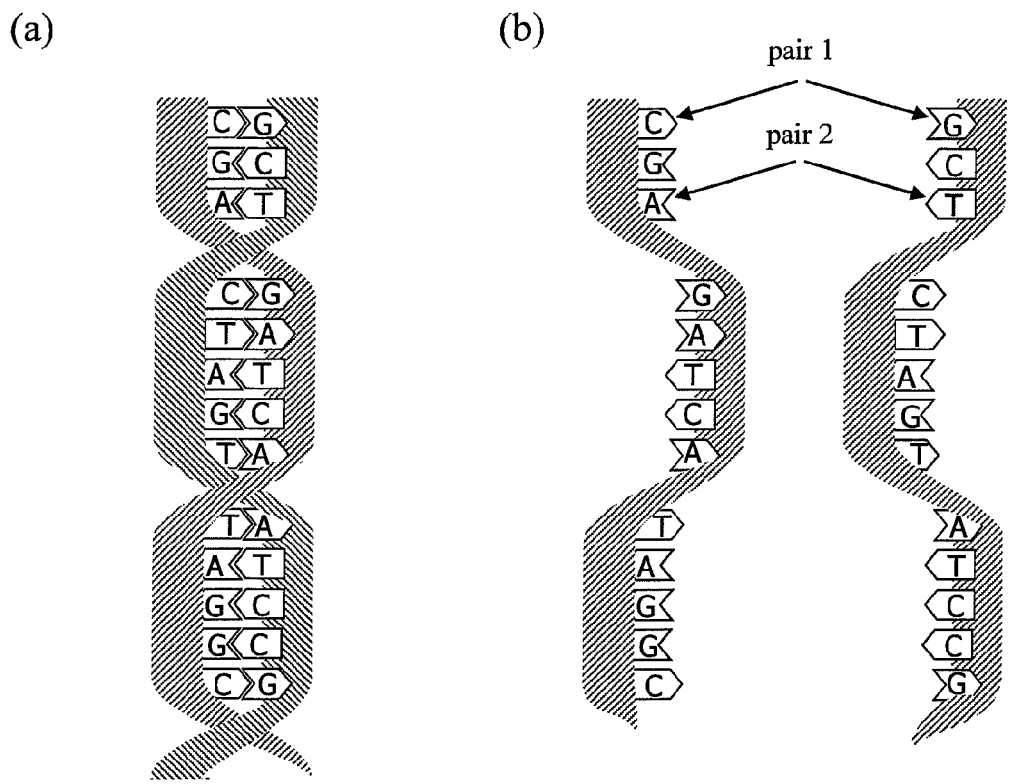
FIG. 11 is a diagram showing that two DNA chains are divided into single chains.

FIG. 11 is a diagram showing that two DNA chains are divided into single chains. FIG. 11 (a) is a diagram showing that a DNA is constructed as a double helix with two chains. FIG. 11 (b) is a diagram showing that the DNA is divided into single chains.

Two DNA chains can be divided into single chains by heats, enzymes, or mechanical forces. The arrangements of two chains are associated with each other. Namely, the four types of bases are coupled as a pair of G and C (pair 1) and a pair of A and T (pair 2). Thus a single chain corresponds to another single chain under this rule.

Figure 12:
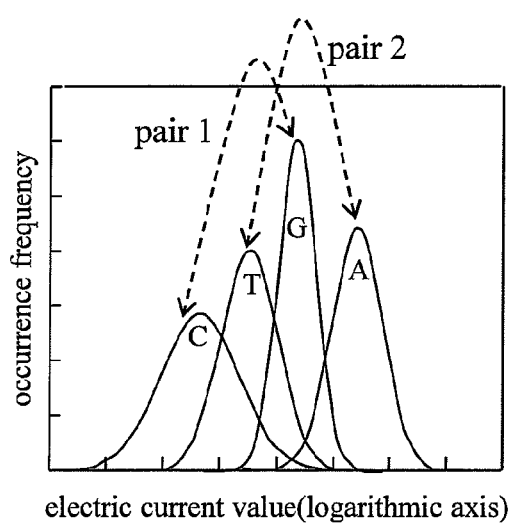
FIG. 12 is a diagram showing a relationship between the electric current distribution of the four bases and the above-described pairs.

FIG. 12 is a diagram showing a relationship between the electric current distribution of the four bases and the above-described pairs. The pair of G and C and the pair of A and T are in the relationship as shown in FIG. 12. According to the relationship shown in FIG. 12, at least four pieces of knowledge listed below are acquired.

(FIG. 12: Knowledge No. 1)

Regarding G and C forming a pair, the electric current of G is larger than that of C. Regarding A and T forming a pair, the electric current of A is larger than that of T. Therefore, when measuring the electric currents of bases forming a pair, the larger one is any one of A or G.

(FIG. 12: Knowledge No. 2)

The two bases with the largest and the second-largest center values of electric currents are A and G. These two bases do not form the pair in the double helix. A is larger than G. The two bases with small center values of electric currents are T and C. These two bases do not form the pair in the double helix. T is larger than C. A and T form a pair and G and C form a pair. Therefore, the pair electric current of A and T is larger than that of G and C.

(FIG. 12: Knowledge No. 3)

Combining the knowledge No. 1 and No. 2, the knowledge below is acquired. Firstly, two nanomolecule paths are provided and two single chain DNAs pass through them respectively, thereby identifying A or G. Next, it is possible to determine which base of A or G has passed through according to the electric current of a single chain or a sum of the electric current values of the pair. By identifying which base of A or G has passed through and by identifying the nanomolecule paths through which the base has passed, it is possible to uniquely determine the type of bases.

(FIG. 12: Knowledge No. 4)

The base A with the maximum center value of electric current and the base C with minimum center value of electric current do not form the pair of the double helix. Therefore, by selecting these bases as the two bases to be read out, the electric voltage difference acquired by integration becomes large. This eliminates the necessity for strictly converging the accumulated electric charge, thereby increasing the processing speed. Depending on electric voltage condition, temperature condition, or acceptable error rate, the trails of distribution does not overlap or the overlap can be ignored. In such cases, the integration may not be necessary and the magnitude relationship may be directly determined. In addition, depending on conditions such as applied voltage, the magnitude relationship between the center value of electric current of T and the center value of electric current of C may be switched to one another. In such cases, the electric current distributions of A and C are large enough, thus the same effect can be achieved.

Figure 13:
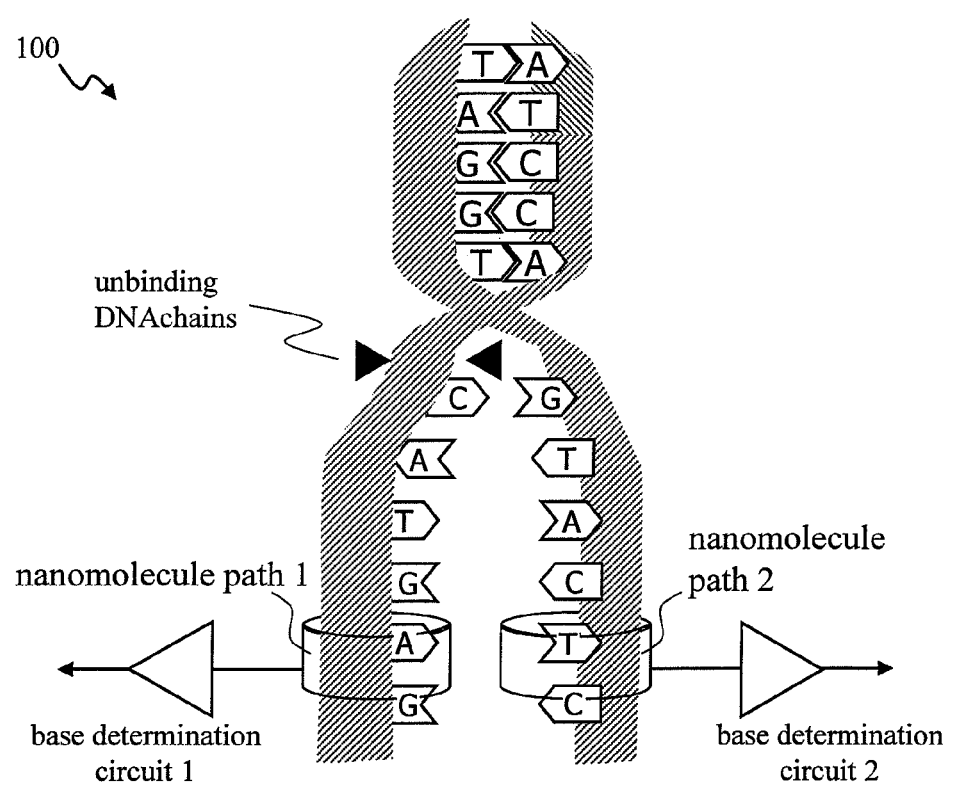
FIG. 13 is a configuration diagram showing around the nanomolecule path of the biomolecule information analysis apparatus 100 according to the embodiment 4.

FIG. 13 is a configuration diagram showing around the nanomolecule path of the biomolecule information analysis apparatus 100 according to the embodiment 4. The biomolecule information analysis apparatus 100 according to the embodiment 4 includes a DNA two chains unbind unit, a nanomolecule path 1, a nanomolecule path 2, a base determination circuit 1, and a base determination circuit 2. Other configurations such as the integration circuit are the same as those of the embodiments 1 to 3, thus description thereof will be omitted.

The DNA two chains unbind unit is a functional unit that unbinds two chains of DNA forming the double helix. For example, enzyme (DNA helicase), heat, or force can be applied to DNA chains to unbind the two chains. A chain in the DNA chains passes through the nanomolecule path 1. Another chain in the DNA chains passes through the nanomolecule path 2. The base determination circuit 1 determines the base using an electric current flowing through an electrode (not shown) included in the nanomolecule path 1. The base determination circuit 2 determines the base using an electric current flowing through an electrode (not shown) included in the nanomolecule path 2.

Figure 14:
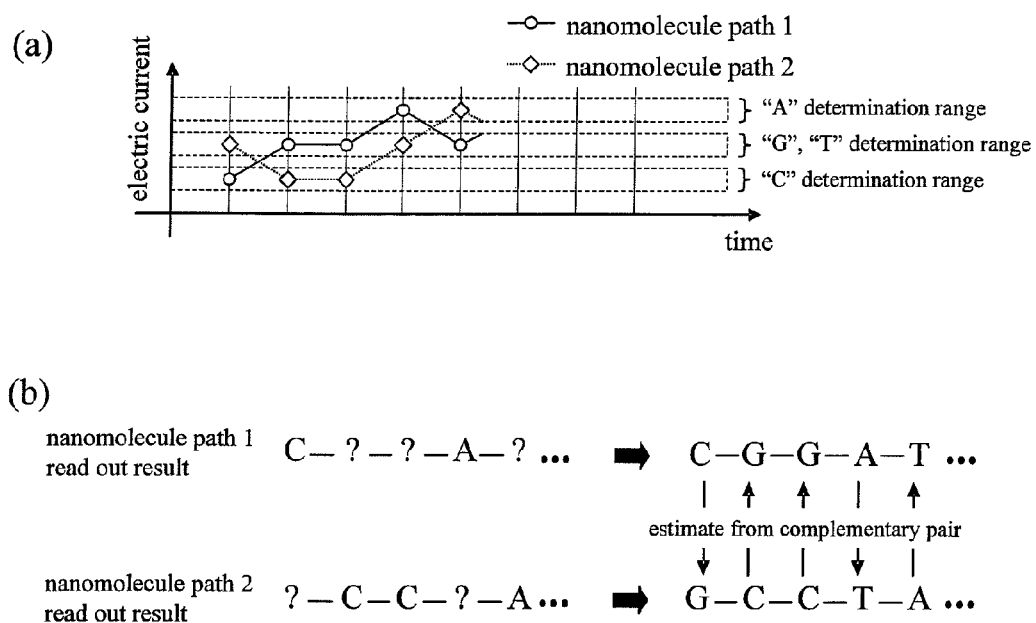
FIG. 14 is a diagram showing that the bases are identified according to the knowledge described with reference to FIG. 12.

FIG. 14 is a diagram showing that the bases are identified according to the knowledge described with reference to FIG. 12. FIG. 14 (a) shows a graph with a horizontal axis indicating time and with a vertical axis indicating electric current value acquired from the two nanomolecule paths or integrated value of the electric current. FIG. 14 (b) shows how to identify the bases using the complementary pairs.

In FIG. 14 (a), electric currents of the bases acquired from the two nanomolecule paths are plotted. A circle is a piece of data corresponding to a base. These electric current values or integrated values thereof have distributions. Therefore, bases A, G, T, and C have respective appropriate ranges for determination. For example, base A has the largest electric current value or integrated value, bases G and T overlap with each other and thus are in the same range, and base C is smaller than them. Thus it is easy to distinguish bases A and C from each other.

The biomolecule information analysis apparatus 100 according to the embodiment 4 can identify bases A or C in each of the nanomolecule paths 1 and 2 respectively. This is shown in FIG. 14 (b) left diagram. It is known that A and T form a pair and C and G form a pair. Therefore, if a base in a pair can be identified, another base in the same pair can also be identified. Accordingly, as shown in FIG. 14 (b) right diagram, the arrangements of each base can be uniquely determined.

Embodiment 4: Summary

As discussed thus far, with the biomolecule information analysis apparatus 100 according to the embodiment 4, it is possible to uniquely identify the base arrangements of DNA by selecting two bases among the four bases from each of two pairs and by identifying the selected two bases. This enables accelerating the processing speed of the biomolecule information analysis apparatus 100.

In addition, if A and C are selected as bases to be identified, the electric voltage difference corresponding to the accumulated electric charge of the integration circuit will be large. Thus it is easy to identify the types of bases, thereby improving analysis accuracy.

Embodiment 5

In an embodiment 5 of the present invention, a specific example of circuit and operation will be described for a configuration that identifies bases according to electric voltage values calculated by summing integrated electric voltages corresponding to bases forming pairs.

Figure 15:
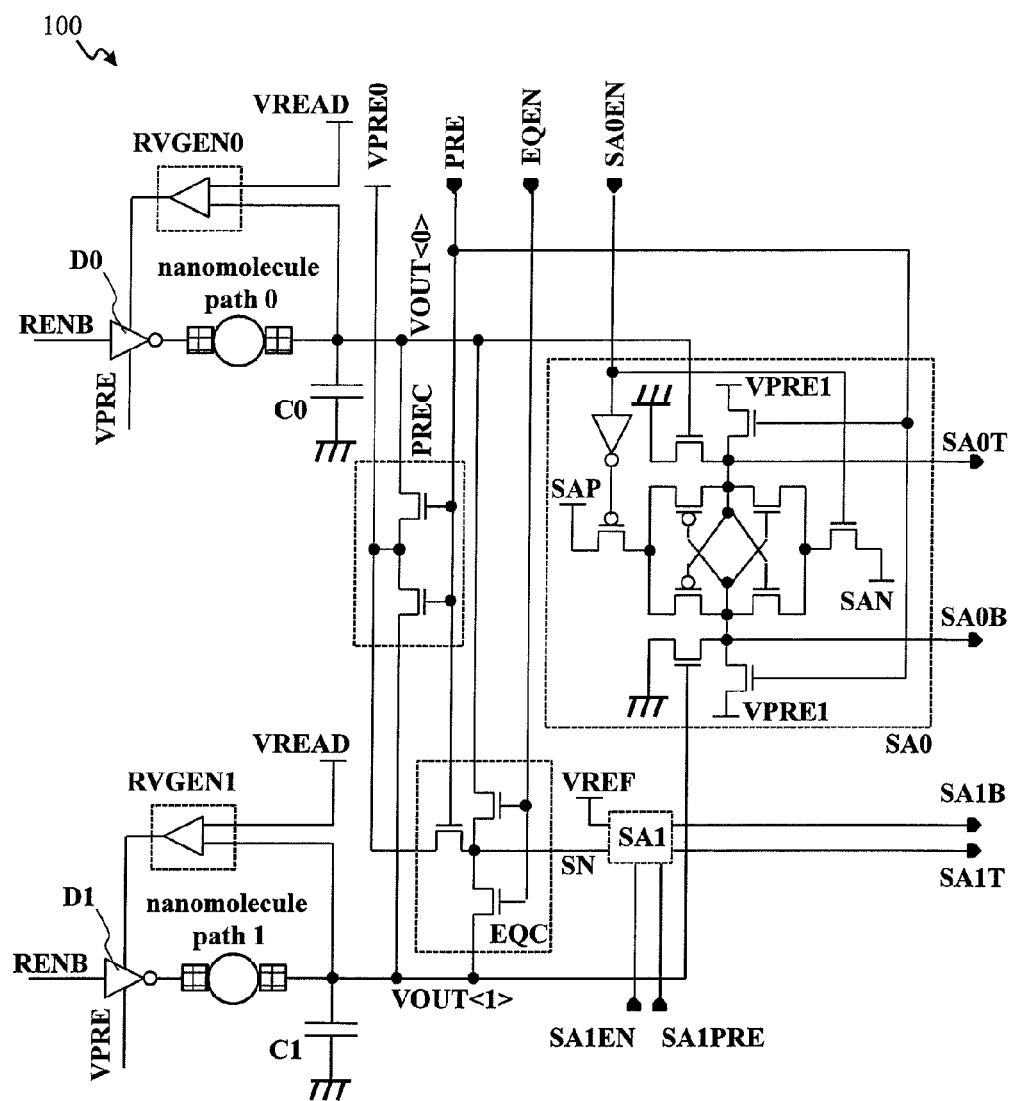
FIG. 15 is a diagram showing a configuration of a biomolecule information analysis apparatus 100 according to the embodiment 5.

FIG. 15 is a diagram showing a configuration of a biomolecule information analysis apparatus 100 according to the embodiment 5. The nanomolecule paths 0 and 1 have electrodes respectively. Each of two single chains unbound from the DNA two chains is inputted into the nanomolecule paths 0 and 1 respectively, as in the embodiment 4.

Drivers D0 and D1 drive each of electrodes of the nanomolecule paths 0 and 1 controlled by the control signal RENB. Bias electric voltage application circuits RVGEN0 and RVGEN 1 are circuits providing bias electric voltages using the bias reference electric voltage VREAD as a power source.

The electrodes of the nanomolecule paths 0 and 1 output outputs VOUT<0> and VOUT<1> respectively. Capacitors C0 and C1 storing electric currents as electric charges are connected to the outputs VOUT<0> and VOUT<1> respectively. The outputs VOUT<0> and VOUT<1> are inputted into the sense amplifier SA0.

A precharge circuit PREC is placed between the outputs VOUT<0> and VOUT<1>. The precharge circuit PREC is controlled by the control signal PRE. The precharge circuit PREC provides the outputs VOUT<0> and VOUT<1> with a value of a precharge voltage power source VPRE0. An equalizing circuit EQC is further disposed between the outputs VOUT<0> and VOUT<1>. The equalizing circuit EQC is controlled by a control signal EQEN. The equalizing circuit EQC outputs an output SN acquired by shorting the outputs VOUT<0> and VOUT<1> and the output SN is inputted into the sense amplifier SA1. The precharge voltage VPRE0 may be input into the short circuit EQC. In this case, the equalizing circuit EQC may provide the output SN with the value of the precharge voltage VPRE0.

The sense amplifier SA0 is controlled by a control signal SA0EN. The circuit configuration of the sense amplifier SA1 is the same as that of the sense amplifier SA0. An input is SN and another input is the reference electric voltage VREF. Power sources SAP and SAN are power sources of the sense amplifier SA0. A control signal SA1EN is a control signal of the sense amplifier SA1. Although the circuit configuration of the sense amplifier SA1 is the same as that of the sense amplifier SA0, the timings of precharge signal are different from those of SA0. Thus a control signal SA1PRE is input. Outputs from the sense amplifier SA0 are SA0T and SA0B. Outputs from the sense amplifier SA1 are SA1T and SA1B.

The sense amplifier SA0 uses VOUT<0> and VOUT<1> as inputs to amplify the difference therebetween. The sense amplifier SA1 uses the signal generated by shorting VOUT<0> and VOUT<1> and the reference electric voltage VREF as inputs to amplify the difference therebetween. According to this configuration, it is possible to identify the magnitude relationship between the base signal of the nanomolecule path 0 outputted to VOUT<0> and the base signal of the nanomolecule path 1 outputted to VOUT<1>. In addition, it is possible to determine whether the sum of the two base signals is larger or smaller than the predetermined reference electric voltage VREF.

If the magnitude of the base signals are in the order of A>G>T>C, A and T are bases forming a pair and A>T, and G and C are bases forming a pair and G>C. The sense amplifier SAO determines whether each of the pair AT and the pair GC passes through the nanomolecule paths 1 or 2. The sense amplifier SA1 determines, under the relationship of A>G>T>C, whether the pair is A+T combining larger signals or the pair is C+G combining smaller signals.

Figure 16:
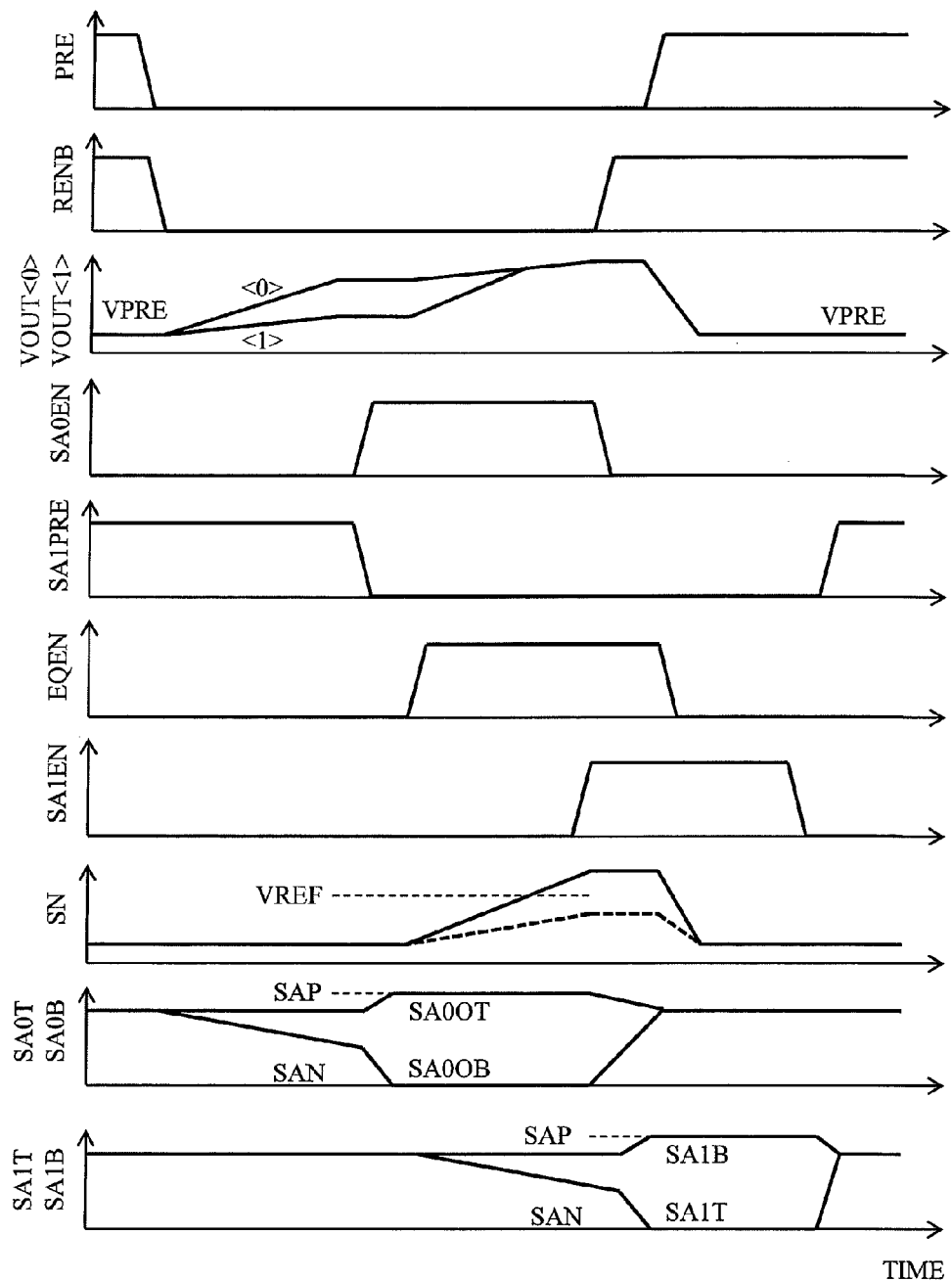
FIG. 16 is a diagram showing an operation example of the biomolecule information analysis apparatus 100 according to the embodiment 5.

FIG. 16 is a diagram showing an operation example of the biomolecule information analysis apparatus 100 according to the embodiment 5. When the precharge is completed, the precharge control signal PRE switches from high level to low level, and the precharge circuit PREC is disconnected from the precharge power source. Next, the control signal RENB that drives the drives D0 and D1 of the electrodes of the nanomolecule paths changes, and an electric voltage is applied to the electrodes of the nanomolecule paths. The capacitor C connected to VOUT<0> and VOUT<1> is charged in accordance with the electric current flowing through the bases passing through the nanomolecule paths, and the electric potential of the capacitor C increases. FIG. 16 shows that an electric current flows into VOUT<0> larger than that of VOUT<1>, and thus the increase in electric potential is large.

The changes in VOUT<0> and VOUT<1> appear in the outputs SA0T and SA0B from the sense amplifier SA0. At this time, the initiation signal SA0EN is inputted into the sense amplifier SA0 to operate the sense amplifier SA0, and the difference between SA0T and SA0B is increased. At this time, the precharge in the sense amplifier SA1 is terminated by the precharge control signal SA1PRE. When sufficient outputs from the sense amplifier SA0 is acquired, the control signal SA1EN changes, and the signal generated by shorting VOUT<0> and VOUT<1> becomes the signal SN to be inputted into the sense amplifier SA1. The sense amplifier SA1 compares the signal SN with the reference electric voltage VREF, and amplifies the comparison result to output as the outputs SA1T and SA1B.

According to the above-described operation, the sense amplifier SA0 amplifies the difference between VOUT<0> and VOUT<1>, and the sense amplifier SA1 amplifies the difference between the signal SN generated by shorting VOUT<0> and VOUT<1> and the reference electric voltage VREF. This enables identifying bases precisely.

Figure 17:
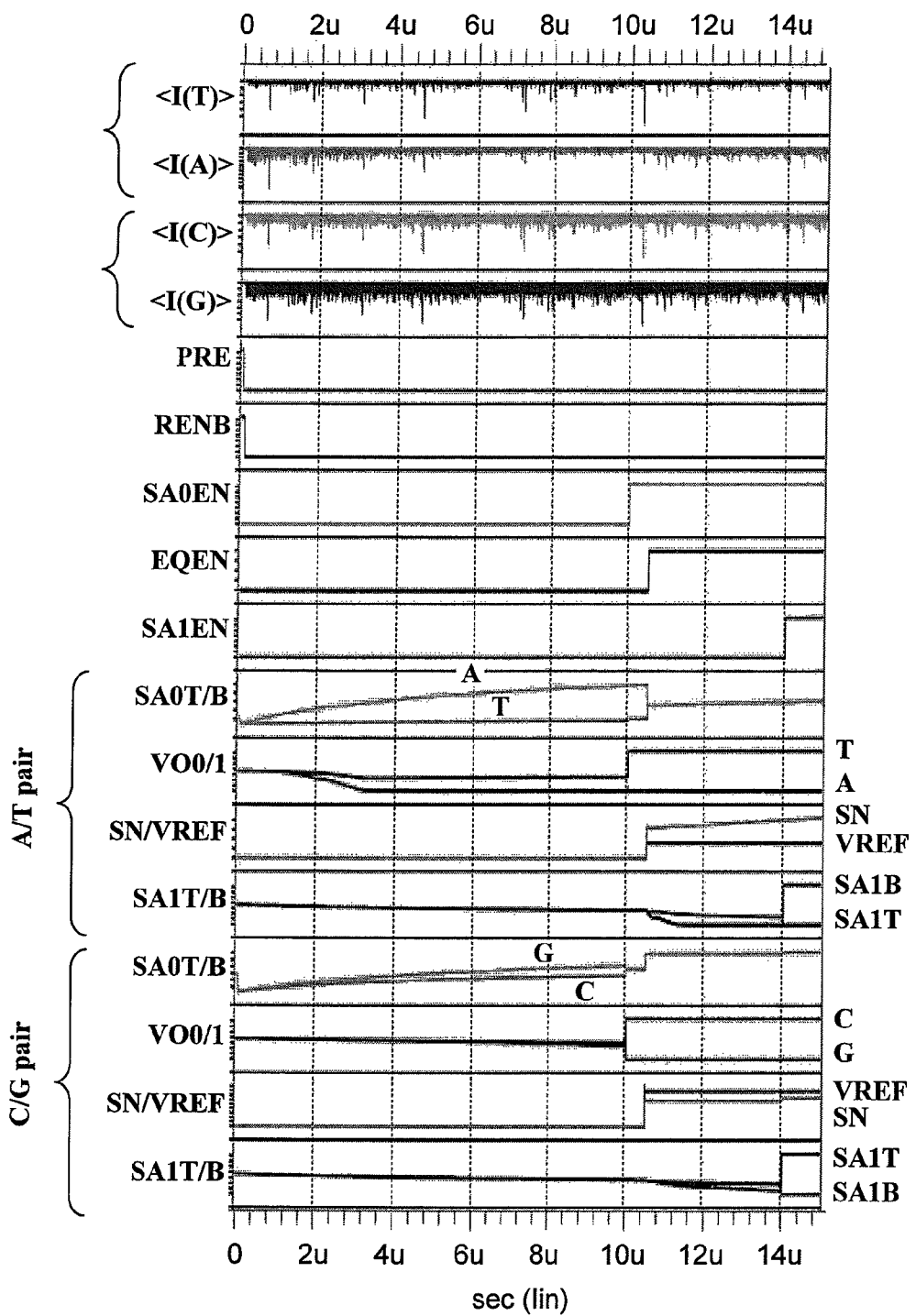
FIG. 17 is a diagram showing an operation example of the biomolecule information analysis apparatus 100 according to the embodiment 5.

FIG. 17 is a diagram showing an operation example of the biomolecule information analysis apparatus 100 according to the embodiment 5. The figure shows a circuit simulation of an operation of the biomolecule information analysis apparatus 100 according to the embodiment 5 using the electric current distribution simulating the electric current distribution flowing through actual bases. It is understood that desired results shown in FIG. 16 are acquired for the waveform of T<I(T)>, the waveform of C<I(C)>, the waveform of G<I(G)>, and the waveform of A <I(A)>.

Embodiment 5: Summary

As discussed thus far, the embodiment 5 describes a specific example of the circuit configuration that identifies base structures using complementary pairs described in the embodiment 4. With the embodiment 5, the same effect as that of the embodiment 4 can be achieved. In addition, it is possible to precisely identify bases by amplifying detection results using the sense amplifiers SA0 and SA1.

Embodiment 6

Figure 18:
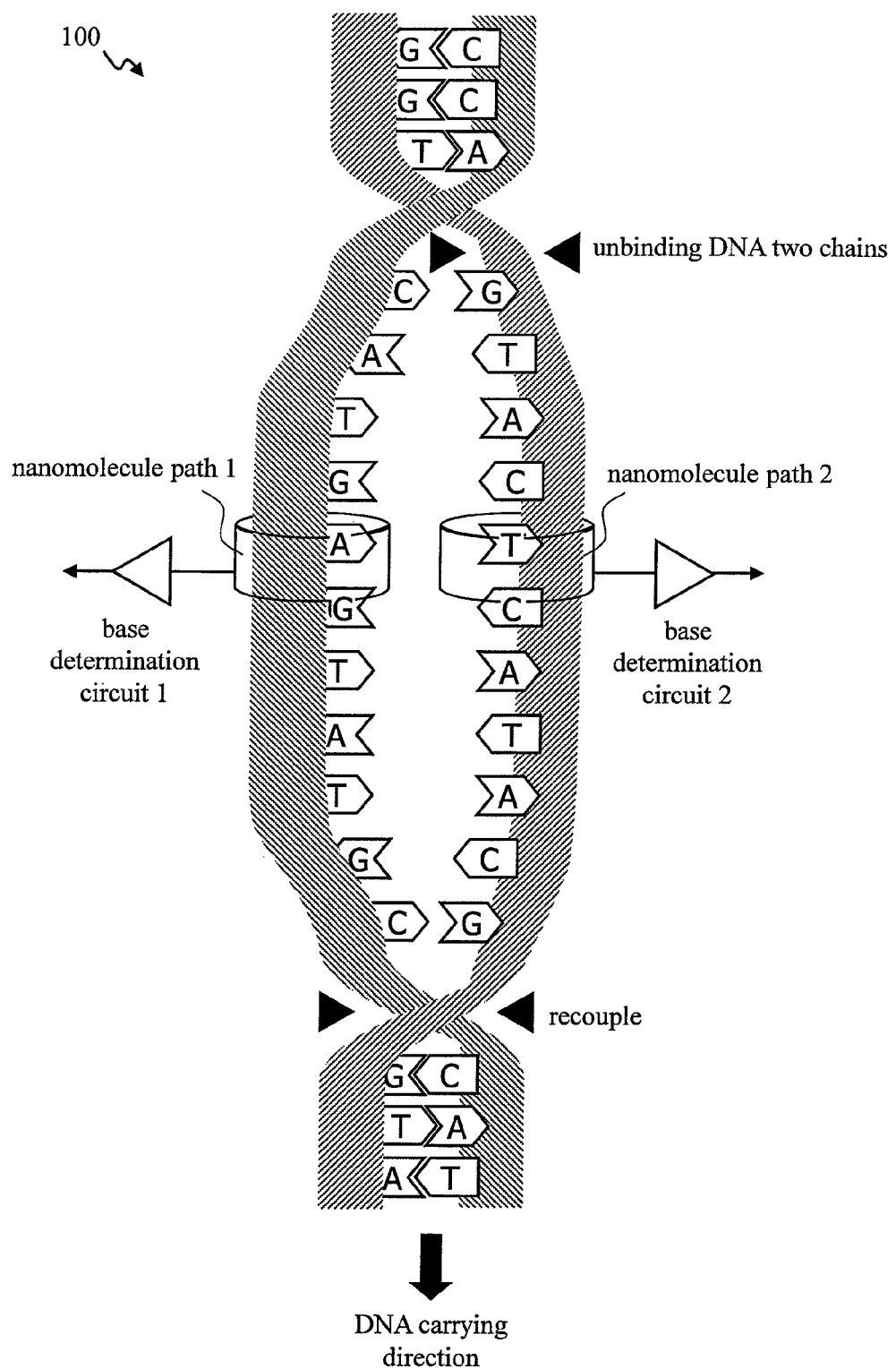
FIG. 18 is a diagram showing configurations around a nanomolecule path of a biomolecule information analysis apparatus 100 according to an embodiment 6.

FIG. 18 is a diagram showing configurations around a nanomolecule path of a biomolecule information analysis apparatus 100 according to an embodiment 6 of the present invention. In the embodiment 6, in addition to the configurations described in the embodiments 4-5, a functional unit that recouples single chains generated by unbinding two chains of DNA is provided. According to the embodiment 6, it is possible to sequentially insert bases pair by pair into two nanomolecule paths. A functional unit that provides the DNA single chains with enzyme can be assumed as the functional unit for recoupling the single chains.

Embodiment 7

Figure 19:
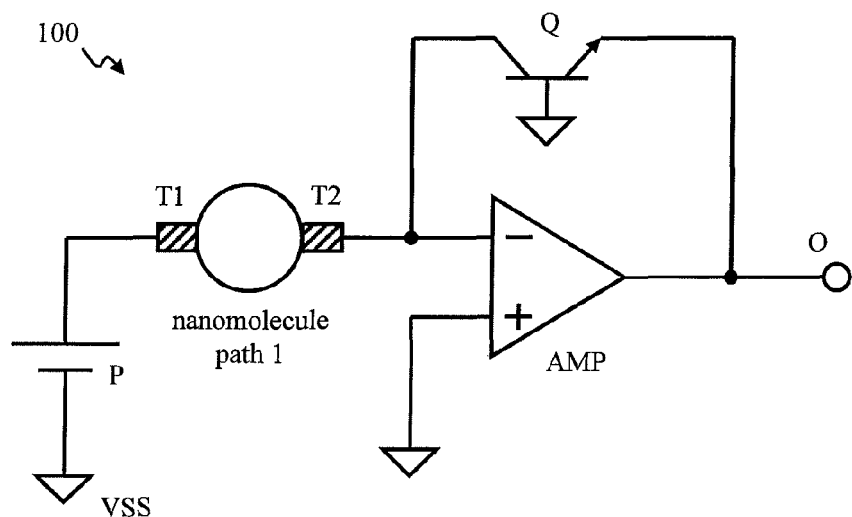
FIG. 19 is a simplified diagram of a circuit configuration of a biomolecule information analysis apparatus 100 according to an embodiment 7.

FIG. 19 is a simplified diagram of a circuit configuration of a biomolecule information analysis apparatus 100 according to an embodiment 7 of the present invention. In FIG. 19, a power source P provides the electrodes T1 and T2 of the nanomolecule path with a bias voltage. An amplifier AMP is an amplifier that amplifies the output from the electrode T2. The amplifier AMP includes a feedback circuit through a base grounding transistor Q and is configured as a nonlinear log amplifier. The output from the electrode T2 has a wide distribution and is amplified by the amplifier AMP after compressed into logarithmic band. By amplifying the output after compressing into logarithmic band, it is possible to precisely amplify signals even with wide distributions.

Figure 20:
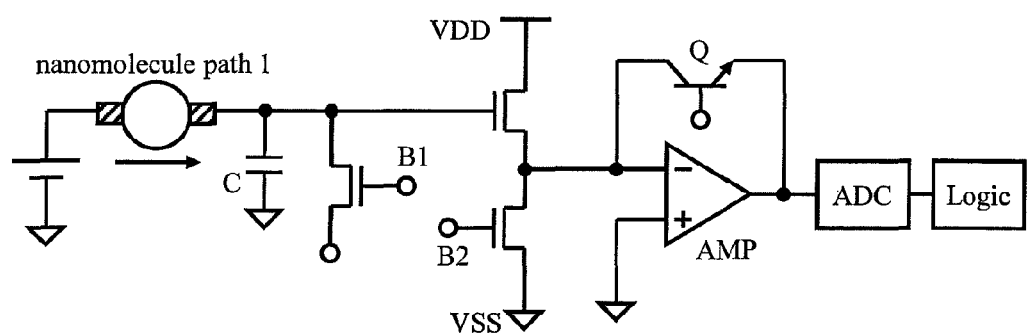
FIG. 20 is a circuit diagram in which an integration circuit is added to the circuit configuration of FIG. 19.

FIG. 20 is a circuit diagram in which an integration circuit is added to the circuit configuration of FIG. 19. The figure also shows an AD converter ADC and the logic circuit LOGIC. In the circuit shown in FIG. 20, a capacitor C and a bias electric current circuit are connected to the electrode of the nanomolecule path. A signal B1 is inputted into the bias electric current circuit. The output from the integration circuit is inputted into the log amplifier AMP. The output from the log amplifier AMP is converted from analog signals into digital signals by the AD converter ADC. The logic circuit LOGIC determines the types of bases.

Figure 21:
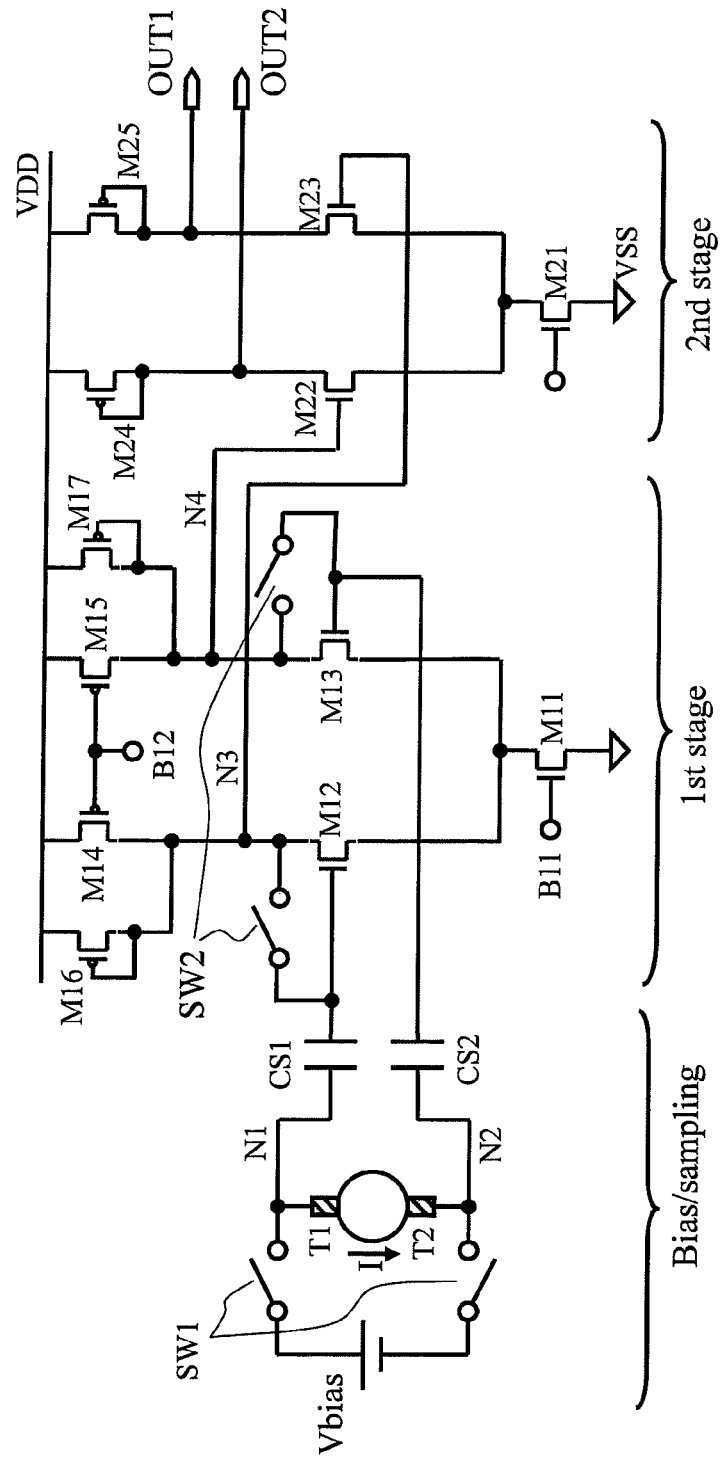
FIG. 21 is a diagram showing a circuit configuration example from the nanomolecule path to the log amplifier AMP in FIG. 20.

FIG. 21 is a diagram showing a circuit configuration example from the nanomolecule path to the log amplifier AMP in FIG. 20. The configuration shown in FIG. 21 does not use, in the IV conversion (current-voltage conversion) circuit portion, amplifiers including general closed loop described later, but uses opened loop.

The circuit configuration shown in FIG. 21 separates the nanomolecule path from the amplification circuit by capacitors CS1 and CS2, and employs a chopper-type amplifier that performs amplification by differential amplifier. According to this configuration, it is not necessary to provide feedback capacitors with small capacitance for closed feedback. This is beneficial in that it is easy to implement the circuit.

The circuit shown in FIG. 21 includes a Bias/sampling unit including the nanomolecule path, a 1st stage detecting microsignals, and a 2nd stage providing a log amplifier. The capacitors CS1 and CS2 separate between the Bias/sampling unit and the 1st stage.

The Bias/sampling unit includes a power source Vbias providing a bias voltage, and a SW1 controlling the connection between the power source Vbias and the electrodes T1 and T2 of the nanomolecule. Terminals N1 and N2 are connected to the capacitors CS1 and CS2 respectively. An electric current I is an electric current flowing between the electrodes T1 and T2.

Under the configuration of the Bias/sampling unit shown in FIG. 21, it is necessary to apply a bias voltage of about 1V to the electrodes T1 and T2 of the nanomolecule path. In this case, a bias voltage difference of 1V is inputted to the differential pair of the differential amplifier circuit comprising the 1st stage and the 2nd stage. If the bias voltage of the input differential pair has a difference of 1V, it is difficult to use the input differential pair in saturated range with good characteristics. Thus the capacitors CS1 and CS2 separate the Bias/sampling unit from the latter stages.

By separating the circuit with the capacitors CS1 and CS2, it is possible to apply the bias voltage Vbias to the electrodes T1 and T2 of the nanomolecule path, and to set the bias point of the latter stage input amplifier at any electric voltage. In addition, by providing a differential amplifier using the two electrodes as inputs, it is possible to double micro electric current components. Further, since the nanomolecule path is manufactured using SiN or the like, it is difficult to manufacture the nanomolecule path in conjunction with usual circuit processes. Thus the circuit around the nanomolecule path may be implemented on a chip different from that of latter stage circuits. However, by separating the circuit by the capacitors CS1 and CS2, it is possible to suppress the influence between such chips.

In the 1st stage unit, a MOS transistor M11 biased by a signal B11 works as an electric current source of the differential amplifier. MOS transistors M12 and M12 are a differential pair of the differential amplifier. MOS transistors M14 and M15 biased by a signal B12 and MOS transistors M16 and M17 connected by diodes are load resistances of the differential pair. N3 and N4 are output terminals of the 1st stage unit.

It is important for an IV conversion circuit detecting micro electric currents to suppress offsets. Specifically, if the amount of offset depends on the magnitude of the tunnel electric current of the nanomolecule path, distortions occur to deteriorate error rates. The embodiment 7 suppresses the distortion using switches SW1 and SW2. The switch SW1 is turned on at first and the switch SW2 is turned on next, thereby suppressing the distortion due to the bias voltage Vbias. The switch SW2 cancels the offset due to threshold variability of the input differential pair M12 and M13.

The 2nd stage unit forms a log amplifier AMP. A MOS transistor M21 biased by a signal B2 works as an electric current source of the differential amplifier. MOS transistors M22 and M23 are a differential pair of the differential amplifier. MOS transistors M24 and M25 are load resistances of the differential pair for utilizing the diode characteristics of MOS. OUT1 and OUT2 are output terminals of the 2nd stage and are connected to the AD converter ADC at the latter stage.

Figure 22:
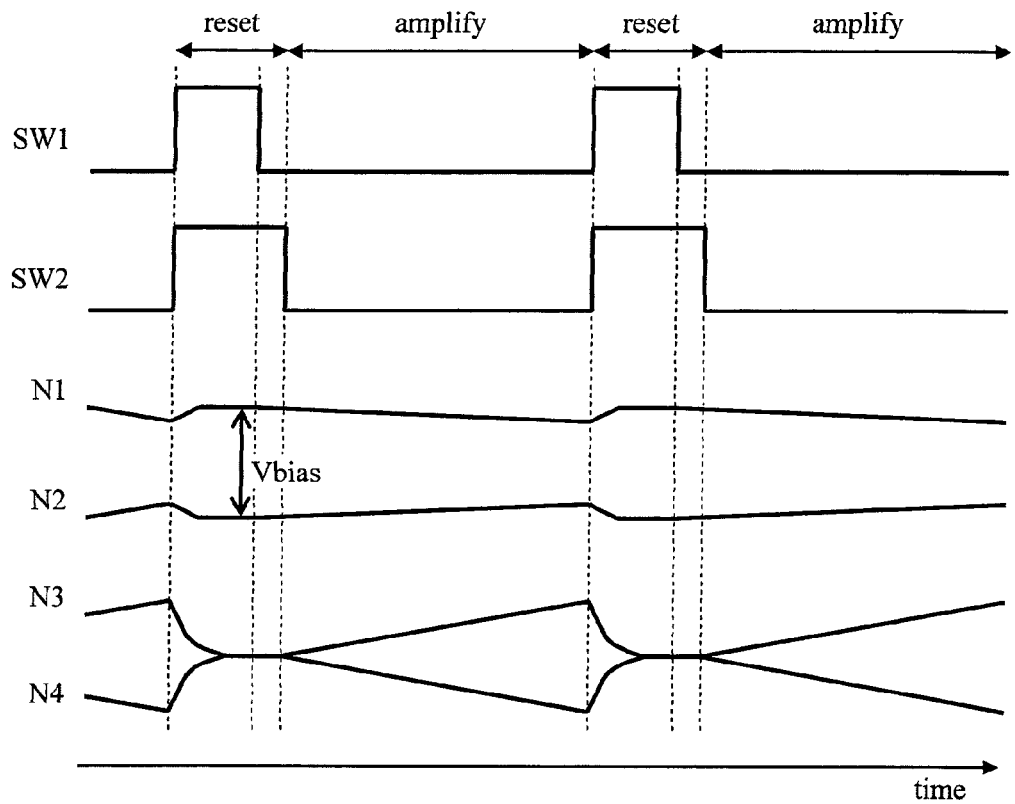
FIG. 22 is a diagram showing an operation example of the Bias/sampling unit and the 1st stage unit in FIG. 21.

FIG. 22 is a diagram showing an operation example of the Bias/sampling unit and the 1st stage unit in FIG. 21. Each operation includes a reset operation term and an amplification operation term.

In the reset operation term, the switch SW1 is turned on at first, and then SW2 is turned on. The bias voltage Vbias appears at the terminals N1 and N2 of the Bias/sampling unit. The electric potentials at N3 and N4 of the 1st stage unit are approximately the same.

In the amplification operation term, the electric potentials of the terminals N1 and N2 vary depending on the electric current flowing through bases. This change in electric potential is inputted into the 1st stage unit through the capacitive coupling by the capacitors CS1 and CS2. As in the reset operation term, the switch SW1 is turned off at first and then the switch SW2 is turned off to operate the differential amplifier AMP. The amplifier AMP amplifies the difference between N1 and N2 to output the outputs N3 and N4. The same operation is repeated.

As discussed thus far, the configuration and the operation of the biomolecule information analysis apparatus 100 according to the embodiment 7 is described. Hereinafter, the advantages of the embodiment 7 will be described with comparing to other configurations.

Figure 23:
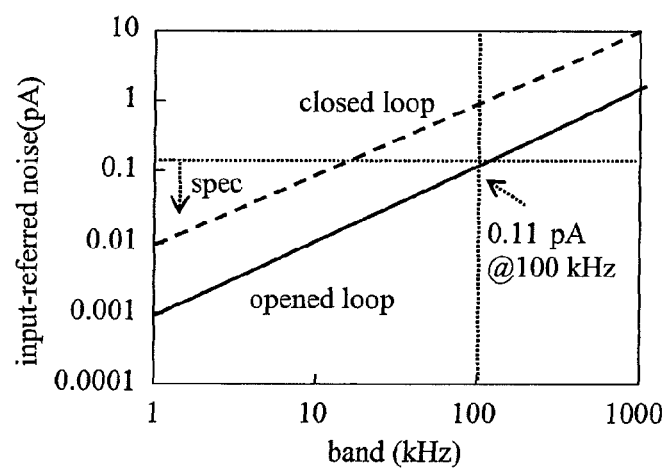
FIG. 23 is a diagram comparing the noise characteristics of opened loop without feedback capacitor with the noise characteristics of closed loop with feedback capacitor.

FIG. 23 is a diagram comparing the noise characteristics of opened loop without feedback capacitor with the noise characteristics of closed loop with feedback capacitor. According to the characteristic example shown in FIG. 23, the input-referred noise at the band of 100 kHz is 0.11 pA. According to the result calculated separately, in order to reduce the read error rate below 0.1%, it is necessary to reduce the input-referred noise below 0.12 pA. The figure shows that the opened loop configuration achieves it.

Figure 24:
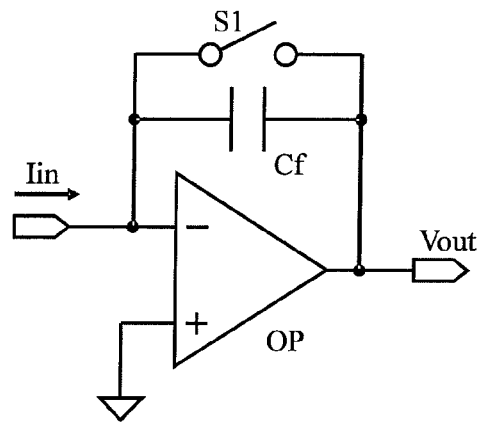
FIG. 24 is a diagram exemplifying an amplifier of closed loop configuration with feedback capacitor.

FIG. 24 is a diagram exemplifying an amplifier of closed loop configuration with feedback capacitor. The amplifier of closed loop configuration shown in FIG. 24 uses an operational amplifier OP to provide an IV conversion circuit. An input current Iin is charged in a capacitor Cf, and is converted into an output voltage Vout using the feedback. If the bandwidth is 100 kHz, it is necessary for this configuration to reduce the feedback capacitor Cf below 0.2 fF in order to suppress the input-referred noise below 0.12 pA.

However, the minimum MIM capacitance that can be manufactured by standard 0.18 μm CMOS process is 20 fF, thus it is not realistic to manufacture a capacitor below 0.2 fF. Microprocess may be used to manufacture a microcapacitor. However, it increases the gate leak current at the CMOS portion and thus it is impossible to detect microcurrents.

Figure 25:
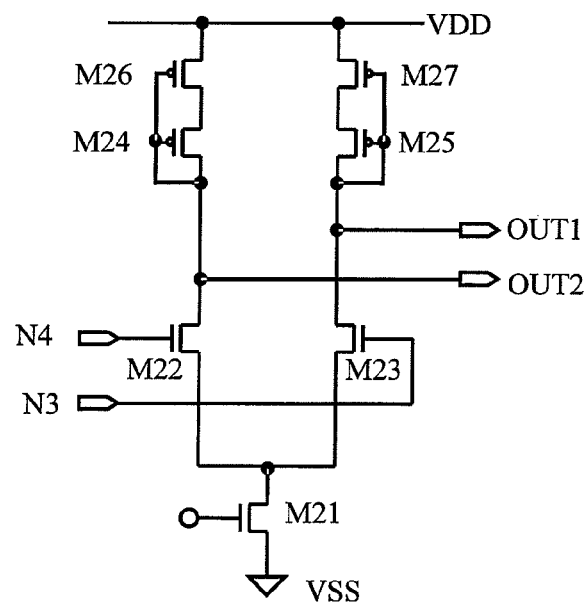
FIG. 25 is a diagram showing another circuit configuration example of the 2nd stage unit.

FIG. 25 is a diagram showing another circuit configuration example of the 2nd stage unit. The circuit configuration shown in FIG. 25 uses the two stage pMOSs connected with diodes as loads, and performs amplification nonlinearly utilizing the diode characteristics of MOS. This enables acquiring output voltages having nonlinear characteristics with respect to the input voltages.

Figure 26:
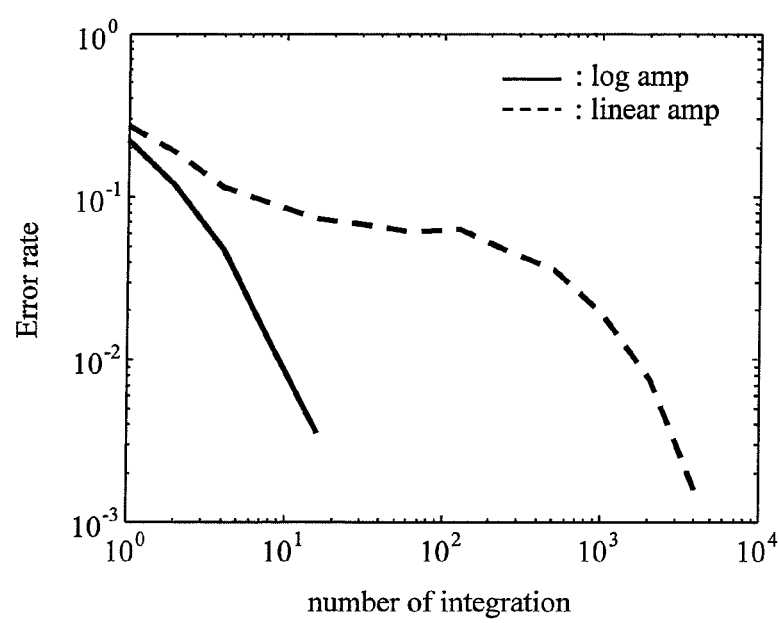
FIG. 26 is a diagram showing a relationship between the read error rate for reading bases and the number of integration for cases where a linear amplifier is employed in the 2nd stage unit and where a log amplifier is employed in the 2nd stage unit, respectively.

FIG. 26 is a diagram showing a relationship between the read error rate for reading bases and the number of integration for cases where a linear amplifier is employed in the 2nd stage unit and where a log amplifier is employed in the 2nd stage unit, respectively. By using a log amplifier, it is possible to significantly reduce the number of integration required to suppress the read error rate.

Embodiment 7: Summary

As discussed thus far, the biomolecule information analysis apparatus 100 according to the embodiment 7 uses a log amplifier in the 2nd stage unit. This enables significantly reducing the number of integration compared to the case where a linear amplifier is used. On the other hand, if a linear amplifier is used, the tunnel current value for each of bases is different by several orders of magnitude. Thus the signal values of bases C or T with small electric current values become relatively small, thereby deteriorating read error rates. Therefore, in the case of using linear amplifier, it is necessary to increase the number of integration in order to precisely detect microcurrents. The embodiment 7 detects microcurrents using a log amplifier having nonlinear characteristics, thereby reducing the number of integration to accelerate the operation of apparatus.

Embodiment 8

In order to measure the micro tunnel current flowing through DNA, it is necessary to use micro nanomolecule path with diameter of about 2 nm. It is difficult to manufacture such a micro nanomolecule path and the manufacturing variation is large. Since the absolute value of the tunnel current significantly depends on the pore diameter of the nanomolecule path, the acquired electric current value is different for each of devices. In addition, the gain of amplifiers varies depending on process, temperature, and power source voltage. Therefore, the acquired tunnel current value varies due to manufacturing variation of nanomolecule path and amplifier gain variation.

If the tunnel current value varies, a gap is caused between the expected electric current distribution and the actually acquired electric current distribution, thereby deteriorating the read error rate. Therefore, in order to precisely determine the types of bases, it is necessary to eliminate the influence from the tunnel current variation due to manufacturing variation of nanomolecule path and amplifier gain variation.

An embodiment 8 of the present invention describes a configuration example that can precisely determine the types of bases even if the acquired absolute values of tunnel currents or amplifier gains are unknown.

FIG. 27 is a diagram showing a configuration of a base type determination logic performed by the logic circuit LOGIC in the embodiment 8. Other configurations of the biomolecule information analysis apparatus 100 are omitted in the figure. FIG. 27 (a) is a functional block diagram for performing the logic. FIG. 27 (b) is a flowchart of the logic.

As shown in FIG. 27 (a), the logic circuit LOGIC stores electric current data corresponding to the detected tunnel currents into a memory. The logic circuit LOGIC sorts the data in accordance with the electric current value as shown in the flowchart of FIG. 27 (b), creates a histogram, and performs a filtering. After the shape of filtered histogram converges, the logic circuit LOGIC sets the threshold for determining the types of four bases according to the local minimum value of the shape. The threshold will be described with reference to FIG. 28 later. The logic circuit LOGIC determines the type of bases using the electric current values stored in the memory according to the threshold.

FIG. 28 is a diagram showing that the electric current distribution changes due to the gain error (gain variation) of the amplifier. FIG. 28 (a) shows an electric current distribution without gain error. FIG. 28 (b) shows an electric current distribution with gain error.

When creating a frequency distribution of the electric current detected by the electrode of the nanomolecule path, the distribution overlaps as described in FIG. 62. Therefore, it is necessary to separate the distribution into four types at each of the distribution peaks as centers of the separated pieces in order to distinguish the type of bases. The threshold values of the electric current for the separation are initialized under the assumption that there is no gain error. Now it is assumed that the threshold values of electric current are R10, R20, and R30 shown in FIG. 28 (a).

If the amplifier has a gain error, the measured electric current distribution varies, thus the distribution borders for each of the four bases appear at positions different from the initial assumption, as shown in FIG. 28 (b). If the initial threshold values R10, R20, and R30 are used unmodified, it is impossible to appropriately distinguish the types of bases.

Then in the embodiment 8, in order to determine whether gain error is included, the logic circuit LOGIC stores the electric current values received from the electrode of the nanomolecule path into the memory to create a histogram of electric current distribution. If the electric current distribution is created with a gain error included, the distribution shows that the gain error is included because the frequency values corresponding to the initial thresholds are different from the assumption. The logic circuit LOGIC can reconfigure the electric current thresholds considering the gain error by reconfiguring the electric current thresholds at positions where the frequency values become sufficiently small, for example.

The variation in the electric current distribution shown in FIG. 28 appears in the integrated result thereof. Therefore, the reference electric voltage VREF for determining the types of bases in accordance with the integration result may be adjusted as in FIG. 28.

Embodiment 8: Summary

As discussed thus far, the biomolecule information analysis apparatus 100 according to the embodiment 8 stores the electric current values detected by the electrode of the nanomolecule path into a storage device, and adjusts the electric current thresholds for separating the electric current distribution into four types in accordance with the stored electric currents. Namely, in the light of possibility that gain errors of amplifiers or manufacturing variations of nanomolecule paths have already occurred, the electric current distribution is distinguished after a certain amount of measurement results has been stored instead of distinguishing the electric current distribution immediately at the time the electric current values are acquired. This enables automatically adjusting the electric current thresholds for distinguishing the type of bases from the electric current distribution in accordance with actual detection results.

Embodiment 9

As described in the embodiment 8, the data acquired from the nanomolecule path varies in performances such as amplifier gains depending on process, temperature, or electric voltage. This may fluctuate the correspondence between the actual distribution of base electric currents and the previously prepared thresholds, causing read error of base types. In addition, since the nanomolecule paths are very small, the manufacturing variations may be large in some cases. Further, it is known that the nanomolecule path deteriorates in characteristics by DNA chains flowing through the nanomolecule path.

In the embodiment 8, the measurement results are accepted without modification but the electric current thresholds for distinguishing the types of bases are adjusted, thereby appropriately distinguishing the type of bases. In an embodiment 9 of the present invention, a configuration example will be described in which the types of bases are distinguished by calibrating the measurement results.

Figure 29:
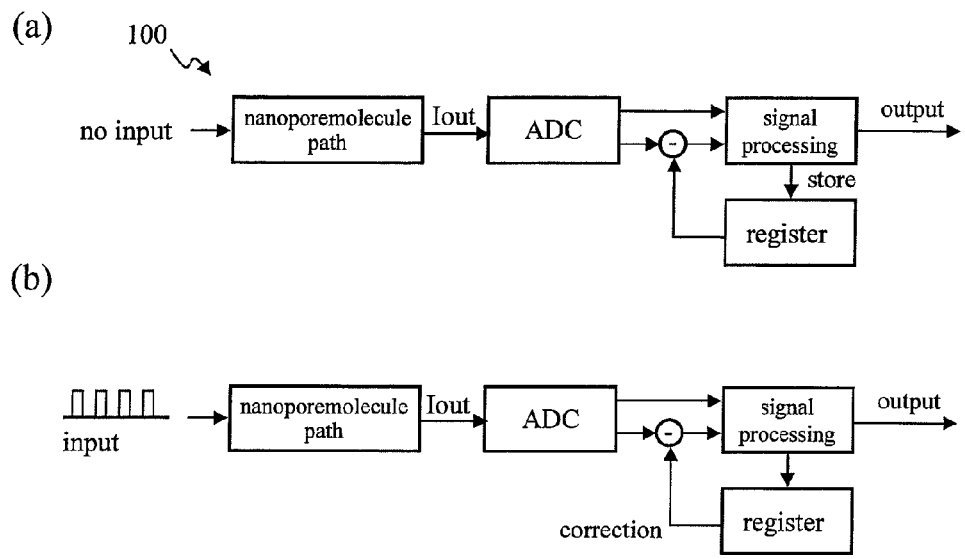
FIG. 29 is a process block diagram describing a process performed by the logic circuit LOGIC of the biomolecule information analysis apparatus 100 according to the embodiment 9.

FIG. 29 is a process block diagram describing a process performed by the logic circuit LOGIC of the biomolecule information analysis apparatus 100 according to the embodiment 9. The configurations other than related to the calibration process are omitted in the figure.

As shown in FIG. 29 (a), the logic circuit LOGIC reads out the electrode signal of the nanomolecule path without input into the nanomolecule path, and converts the signal into digital signal to store in the register. The data stored into the register includes information about characteristics of the nanomolecule path used for measurement, medium, temperature, and the like.

As shown in FIG. 29 (a), the logic circuit LOGIC, when a base enters the nanomolecule path, measures the signals from the actual base, and then corrects the variation components without input into the nanomolecule path. This enables eliminating, from the actual measurement result, variation components due to characteristics of the nanomolecule path, medium, or temperature. According to the above-described process, it is possible to precisely determine the type of bases even if variations due to process, temperature, or electric voltage are included.

The process shown in FIG. 29 (a) (b) may be performed in chronological order or may be performed simultaneously. If performed simultaneously, the register may be shared in each process. Alternatively, the register may be divided into areas for each of the processes, and the processed data may be transferred sequentially.

Figure 30:
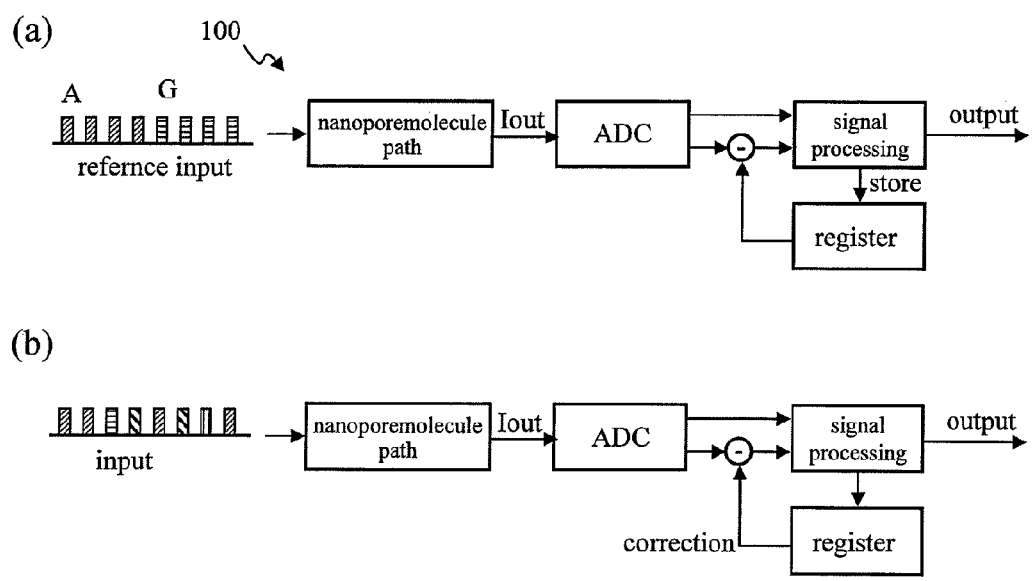
FIG. 30 is a diagram showing another configuration example for performing the calibration process.

FIG. 30 is a diagram showing another configuration example for performing the calibration process. The process performed by the logic circuit LOGIC is approximately the same as that of FIG. 29. However, a reference input is inputted into the nanomolecule path before the actual bases are measured.

As shown in FIG. 30 (a), the logic circuit LOGIC measures the electric current using the bases having known arrangements as the reference input into the nanomolecule path. In the example shown in FIG. 30 (a), four bases A are inputted followed by four bases G. Appropriate bases as the reference input are, for example, bases including a certain number of the same consecutive bases, or bases including periodically repeated base orders such as ATGC. The measured data includes information about characteristics of the nanomolecule path used for measurement, medium, temperature, and the like.

When bases enter the nanomolecule path, the logic circuit LOGIC performs the same process as in FIG. 29 (b). This enables eliminating the variations as in FIG. 29.

FIG. 31 is a diagram showing another configuration example of the bases used as the reference input. As shown in FIG. 31 (a), it is possible to attach bases having known arrangements as a reference portion before bases to be inspected. FIG. 31 (b) shows a configuration of the processing unit for the calibration process.

Embodiment 9: Summary

As discussed thus far, the biomolecule information analysis apparatus 100 according to the embodiment 9 calibrates the base electric currents outputted from the electrode of the nanomolecule path, and determines the type of bases using the calibration result. This enables eliminating the influence of variations due to characteristics of the nanomolecule path and the like, thereby precisely determining the type of bases.

Embodiment 10

In an embodiment 10 of the present invention, a configuration example will be described in which the configuration of nanomolecule path is improved to achieve accelerated and high-precision base determination.

FIG. 32 is a diagram showing a configuration of the nanomolecule path in the embodiment 10. In the embodiment 10, multiple pairs of electrodes are disposed at the nanomolecule path. The electrodes include two types of them. Electrodes T11 and T12, T21 and T22, and T31 and T32 are electrode pairs detecting electric currents flowing through the bases. Electrodes S11 and S12, S21 and S22, and S31 and S32 are electrodes used for carrying DNA chains within the nanomolecule path.

By providing multiple detection electrodes, it is possible to simultaneously acquire electric currents in which different bias voltages are used. The electric currents from the bases have voltage dependencies that are different for each of bases ATGC. By simultaneously acquiring electric currents in which different voltages are used, it is possible to improve the precision for distinguishing the bases.

In addition, when performing measurement using pulses, the pulse width influences on the detection results and has dependencies that are different for each of the bases ATGC. Namely, the frequency characteristics of electric current response are different for each of the bases. By using multiple electrodes, it is possible to simultaneously perform measurements using different pulse widths to acquire the detection results simultaneously. This enables improving the precision for distinguishing the bases.

For example, the electrodes S21 and S22 may be provides with electric voltages that are opposite to those for the pair of the electrodes S11 and S12 and the pair of the electrodes S31 and S32. This enables creating an electric potential recess at the electrodes S21 and S22. Since each of bases has electrical characteristics, a specific base may be sandwiched in the electric potential recess to control the flow of bases.

In addition, it is possible to control the progress of bases by applying global electric fields using other electrodes not shown in the figure. Using the sandwiching by the electric potential recess along with the flow control enables carrying the DNA chain bases one by one, for example.

Note that the two electrodes are disposed separately, for the sake of explanation. However, some of the electrodes may include the two functions in one electrode.

Embodiment 10: Summary

As discussed thus far, the biomolecule information analysis apparatus 100 according to the embodiment 10 can improve precision or speed for distinguishing the DNS chain bases and can control carrying the DNS chains as desired by detailed control of DNA flows using multiple electrodes.

Embodiment 11

FIG. 33 is a diagram showing a configuration example of the nanomolecule path in an embodiment 11 of the present invention. The figure shows an example in which electrodes oriented to multiple directions are disposed around the nanomolecule path formed as a through hole.

In FIG. 33 (a), a pair of electrodes T21 and T22 is provided, in the nanomolecule path, in the direction perpendicular to a pair of electrodes T11 and T12. This enables acquiring the electric current signals in two directions simultaneously. In FIG. 33 (b), a pair of electrodes S11 and S12 for carrying the DNA chain bases is provided in the direction perpendicular to a pair of electrodes T11 and T12 for acquiring electric current signals. This enables providing, using the electrodes S11 and S12, electric fields by which signals larger than the bases are acquired and acquiring the electric current signals when applying the electric fields.

FIG. 34 is a diagram showing a configuration example in which multiple electrodes are disposed in the thickness direction of the nanomolecule path formed as a through hole. When a DNA proceeds along the arrow direction in the nanomolecule path in FIG. 34, the electrodes S11 and S12 and the electrodes S21 and S22 work as pairs respectively or the four electrodes work together to apply electric voltages. It applies electric fields to the DNA chains and the bases connected to the DNA chains, thereby controlling direction and orientation of the DNA chains, position and inclination of the DNA chains with respect to the center of the nanomolecule path, or movement of the DNA chains. Electrodes T11 and T12 for detecting electric currents flowing through the bases are disposed at downstream of the proceeding direction of DNA.

Figure 35:
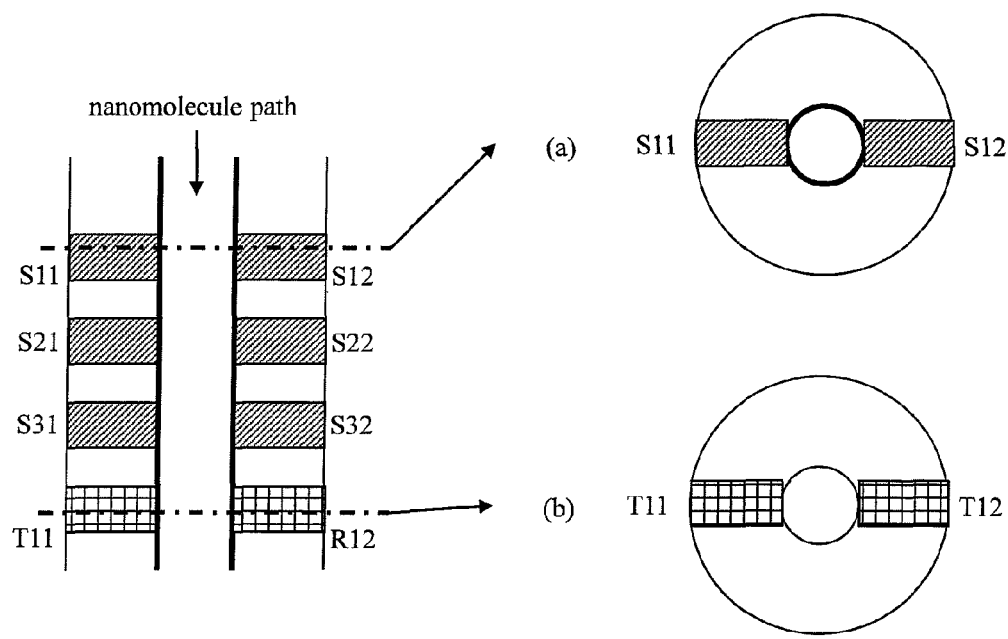
FIG. 35 is a diagram showing a configuration example in which multiple electrodes for carrying the DNA chains are provided in the thickness direction.

FIG. 35 is a diagram showing a configuration example in which multiple electrodes for carrying the DNA chains are provided in the thickness direction. In FIG. 35, electrodes S11 and S12, S21 and S22, and S31 and S32 for carrying DNA chains are disposed in the thickness direction. In addition, electrodes T11 and T12 for detecting electric currents are disposed downstream or upstream of the six electrodes.

Figure 36:
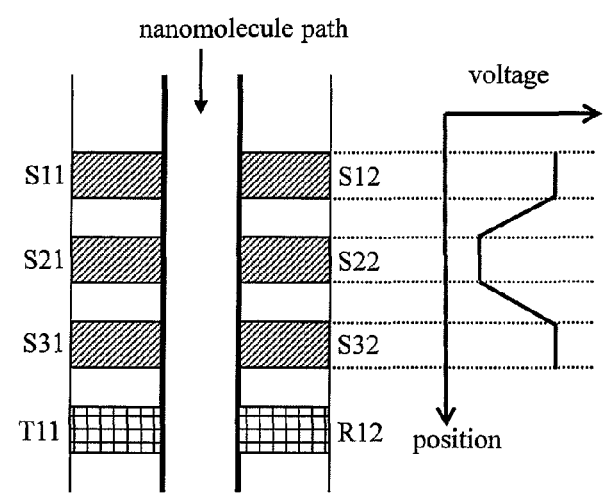
FIG. 36 is a diagram showing electric voltages formed within the nanomolecule path shown in FIG. 35.

FIG. 36 is a diagram showing electric voltages formed within the nanomolecule path shown in FIG. 35. For example, the electrodes S21 and S22 are provided with electric voltages opposite to those for the pair of the electrodes S11 and S12 and the pair of the electrodes S31 and S32, thereby creating an electric potential recess at the electrode S21 and S22. This enables achieving the same effect of carrying DNA chains as described in the embodiment 10.

Figure 37:
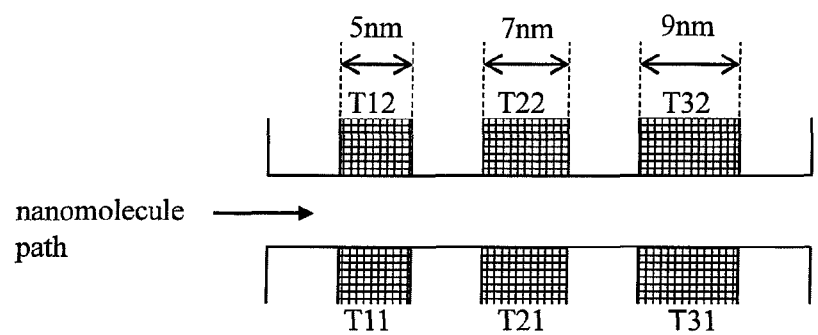
FIG. 37 is a diagram showing another configuration of electrodes detecting the electric currents flowing through the bases.

FIG. 37 is a diagram showing another configuration of electrodes detecting the electric currents flowing through the bases. This nanomolecule path may be formed as a hole provided in a substrate or may be formed as a gap or a path on a substrate.

In the example shown in FIG. 37, the thicknesses of electrodes T11 and T12, T21 and T22, and T31 and T32 for detecting electric currents flowing through the bases are different from each other. In this example, each of the thickness is 5 nm, 7 nm, and 9 nm respectively.

According to the configuration example shown in FIG. 37, even in cases where it is difficult to independently manufacture electrodes with thickness of 2 nm, for example, due to manufacturing techniques, electrical characteristics, or reliability characteristics, it is possible to acquire data equivalent to 2 nm electrodes using the thickness differences of each electrode. Namely, by acquiring the data of the electrodes T11 and T12 with thickness of 5 nm and acquiring the data of the electrodes T21 and T22 with thickness of 7 nm after desired time has passed from the former acquisition, the difference of the two acquisitions is equivalent to the data acquired by using electrodes with thickness of 2 nm. Any number of types of electrodes may be used. Electrodes for controlling carriage of DNA chains may be provided before or after the electrodes. Alternatively, the electrodes T11 to T13 may perform the carry control.

Embodiment 10: Summary

As discussed thus far, the biomolecule information analysis apparatus 100 according to the embodiment 11 provides multiple electrodes around the nanomolecule path, and each of the electrodes may have different roles. This enables detailed control of DNA chains within the nanomolecule path or precise detection of base electric currents.

Embodiment 12

Figure 38:
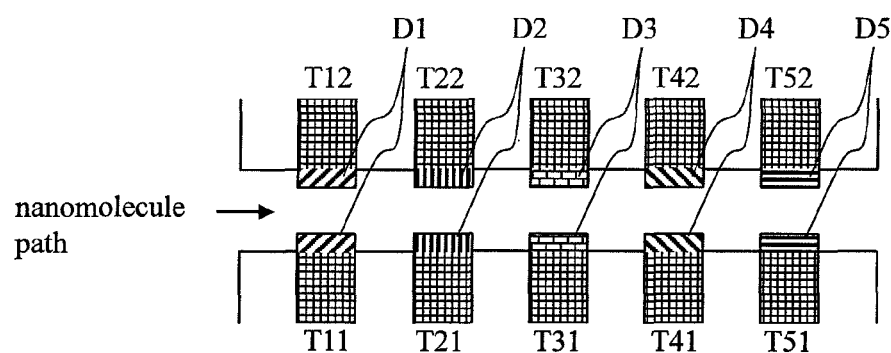
FIG. 38 is a diagram showing a configuration example of the nanomolecule path in an embodiment 12.

FIG. 38 is a diagram showing a configuration example of the nanomolecule path in an embodiment 12 of the present invention. In the embodiment 12, specific metals or polymers D1 to D5 reacting to each of the bases are attached to the electrodes T11 to T52 for detecting electric currents flowing through the bases. D1-D5 are materials that specifically react to specific bases or multiple bases or materials that increases the electric current flowing through the bases. According to the configuration example shown in FIG. 38, it is possible to provide electrodes that effectively react to specific bases, thereby more precisely determining the type of bases.

Figure 39:
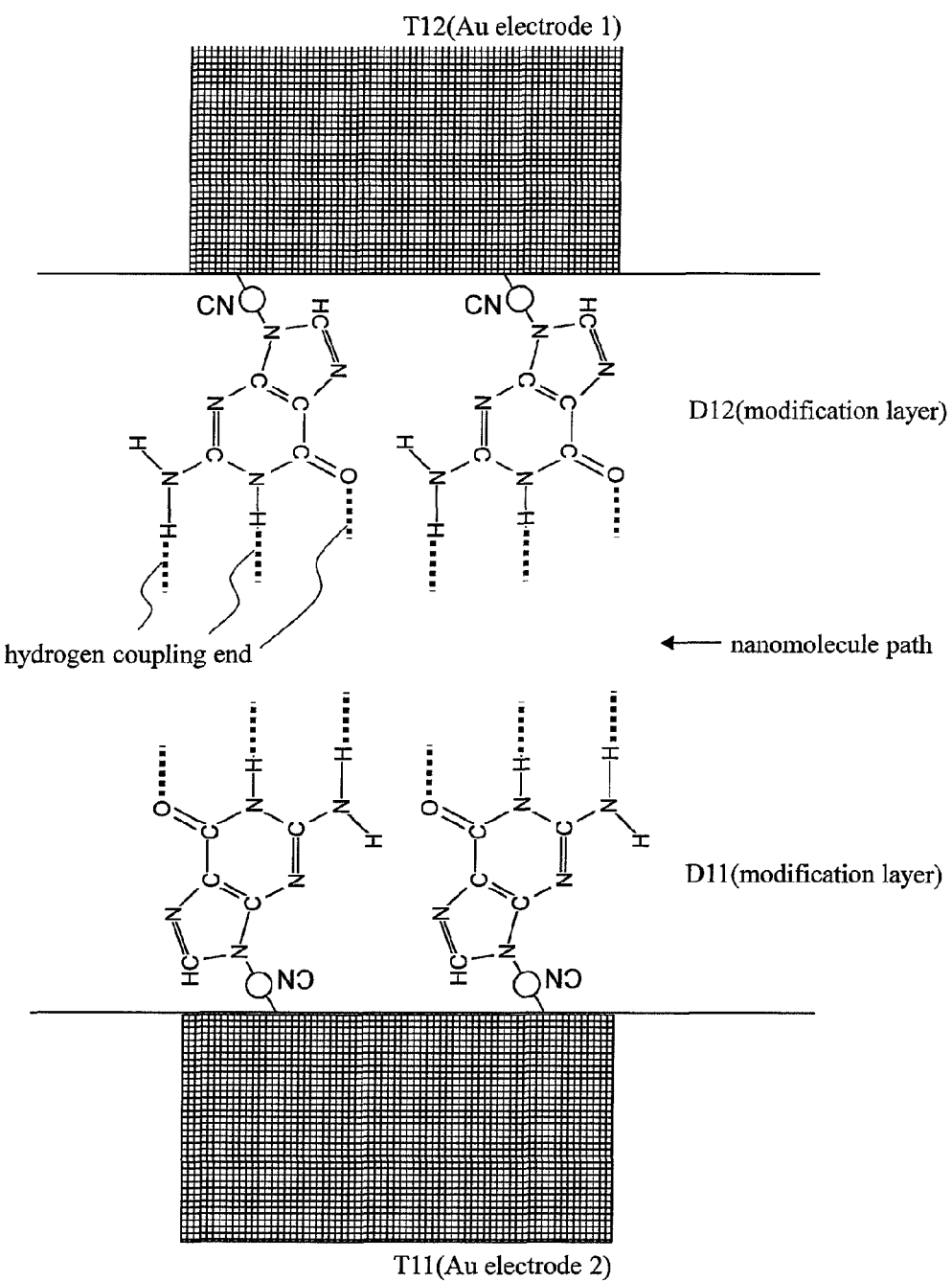
FIG. 39 is a diagram showing an example of the materials D1-D5 shown in FIG. 38.

FIG. 39 is a diagram showing an example of the material D1-D5 shown in FIG. 38. In this example, a sectional view of a pair of electrodes in a nanomolecule path is shown. Actually, the electrode extends in the vertical direction with respect to the paper. The nanomolecule path may be formed as a hole provided in a substrate or may be formed by disposing two electrodes with a narrow gap on a substrate.

In the example shown in FIG. 39, the specific metals or polymers reacting to the bases are referred to as modification layers D11 and D12 modifying the electrodes T12 and T12. The electrodes T11 and T12 are formed with Au, for example. The materials D11 and D12 are examples of polymers that are highly likely to be hydrogen-coupled with specific bases. CN is an atom or a molecule that is inserted so as to accelerate the coupling of the polymer with metal electrodes.

When a base that is highly likely to couple with the materials D11 or D12 passes through the nanomolecule path, the base and the materials D11 or D12 are transiently coupled to cause large electric currents to flow. This enables identifying the type of base close to the electrode. If the modification layers D11 and D12 are formed with the same material, it is possible to acquire large base electric currents independently from orientations and positions of the base within the nanomolecule path.

Figure 40:
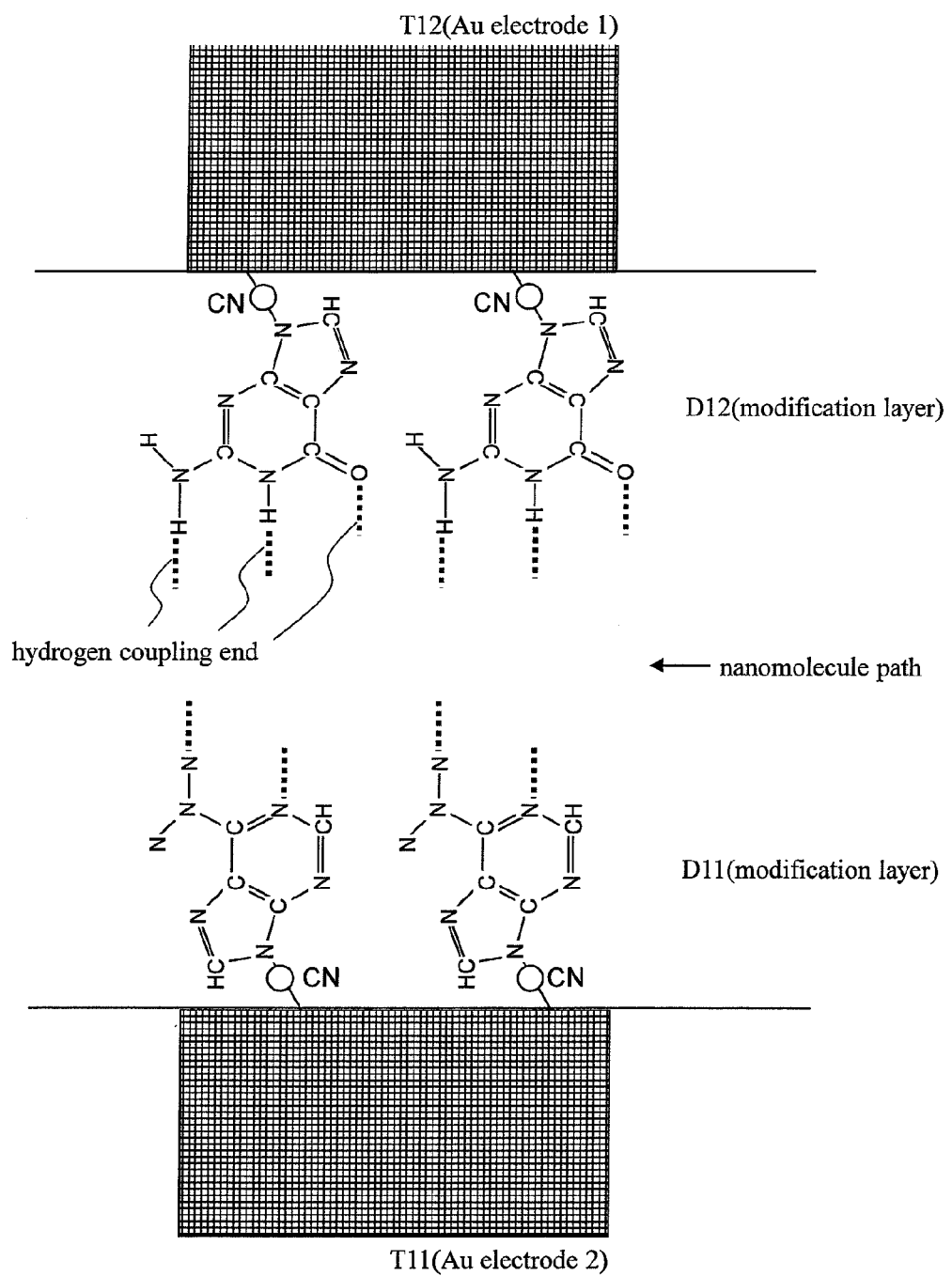
FIG. 40 is a diagram showing an example where the modification layers D11 and D12 are formed with different materials.

FIG. 40 is a diagram showing an example where the modification layers D11 and D12 are formed with different materials. In this case, it is possible to acquire large electric currents when consecutive bases flow in specific order. In addition, the configuration shown in FIG. 40 is also effective in cases where only a base in one pair is required to be identified. Further, a modification layer that is likely to react to multiple base types may be provided at both of the electrodes T11 and T12. In this case, large base electric current can be acquired when the consecutive base arrangement pattern matches with the arrangement of the modification layer, for example.

Figure 41:
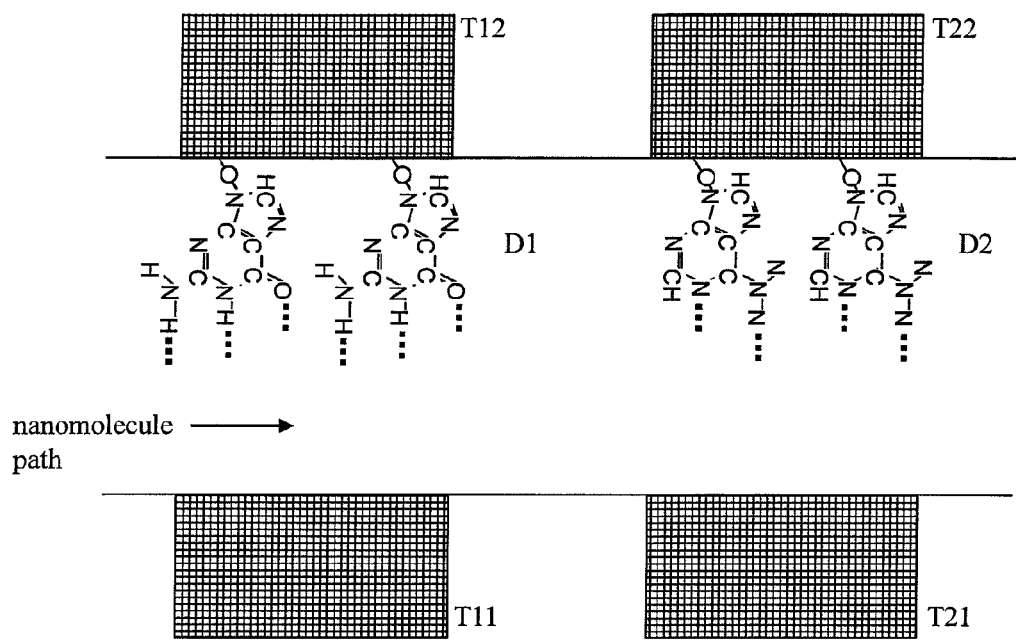
FIG. 41 is a diagram showing an example where multiple of electrodes and modification layers are provided in the nanomolecule path.

FIG. 41 is a diagram showing an example where multiple of electrodes and modification layers are provided in the nanomolecule path. Electrodes for controlling carriage of DNA chains may be provided before or after the electrodes. In FIG. 41, the material D1 provided for the pair of the electrodes T11 and T12 is different from the material D2 provided for the pair of the electrodes T21 and T22. The bases easily detected by the materials D1 and D2 are different from each other. For example, four electrodes corresponding to the four bases ATGC may be provided.

In FIG. 41, the materials D1 and D2 are provided only for the electrodes T12 and T22 at one side. However, the materials D1 and D2 may be provided at the side of the electrodes T11 and T21. In addition, as shown in FIG. 40, the electrodes in a pair may each have different modification layers.

Figure 42:
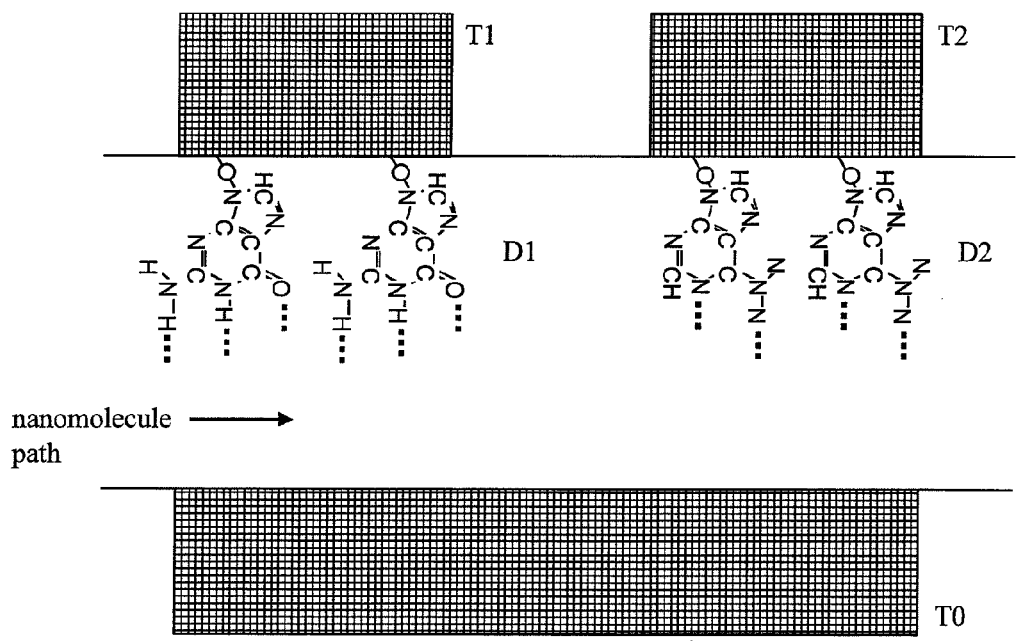
FIG. 42 is a diagram showing a configuration example modifying one of the electrodes in a pair as a common electrode.

FIG. 42 is a diagram showing a configuration example modifying one of the electrodes in a pair as a common electrode. In this example, the electrodes T1 and T2 are both paired with a common electrode T0. Depending on the structure of the nanomolecule path, it is easier to form the nanomolecule path using the common electrode than other configurations. In such cases, the configuration shown in FIG. 42 is effective.

Embodiment 12: Summary

As discussed thus far, the biomolecule information analysis apparatus 100 according to the embodiment 12 disposes materials that are likely to react to specific bases at the electrodes. This enables precisely determining the type of bases.

Embodiment 13

FIG. 43 (a) (b) is a diagram showing a distribution of base electric currents in cases where the bias voltages are 0.1 V and 1 V respectively. Depending on the type of bases ATGC, the center electric current value ($\mu$) and the half-value width ($\sigma$) are different.

FIG. 44 is a diagram showing that the distribution of the base electric current varies depending on temperature. FIG.

44 (*a*) shows a variation example of the center electric current value (μ). FIG. 44 (*b*) shows a variation example of the half-value width (σ). In addition, the distribution of the base electric currents varies depending on pulse widths or alternating frequencies used for measurement.

Figure 45:
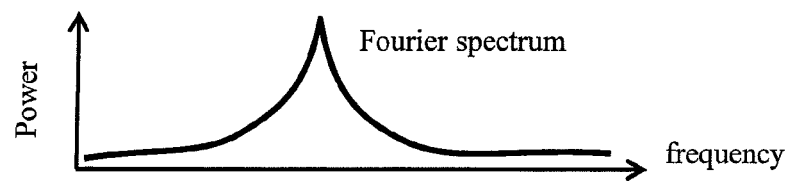
FIG. 45 is a diagram showing a voltage frequency when the base electric current output becomes maximum.
Figure 46:
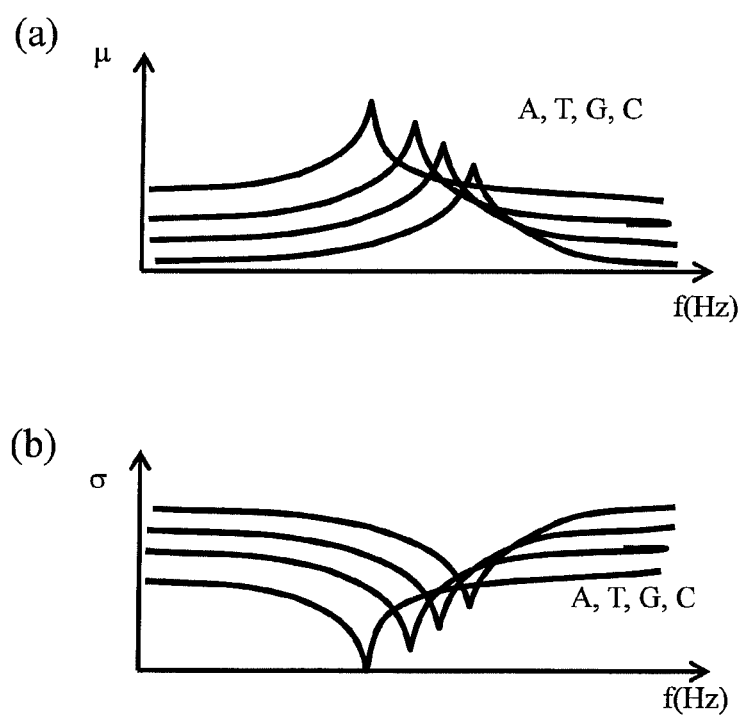
FIG. 46 is a diagram showing that the voltage frequencies that provide the maximum base electric current output are different for each of the type of bases.

FIG. 45 is a diagram showing a voltage frequency when the base electric current output becomes maximum. FIG. 46 is a diagram showing that the voltage frequencies that provide the maximum base electric current output are different for each of the type of bases. As shown in FIG. 46, the center electric current value (μ), the pulse width of half-value width (σ) of the distribution, and the response to alternating frequency are different for each of the bases.

According to FIGS. 43-46, various differences of the detection results occur depending on the type of bases. The biomolecule information analysis apparatus 100 may positively utilize the difference for each of bases shown in FIG. 46 to decide electrode positions or application voltages, to integrate electric currents, and to provide highly sensitive amplifiers.

Embodiment 14

In an embodiment 14 of the present invention, a specific configuration example of the biomolecule information analysis apparatus 100 will be described. Configurations that are already described in the prior embodiments will be omitted in the description.

Figure 47:
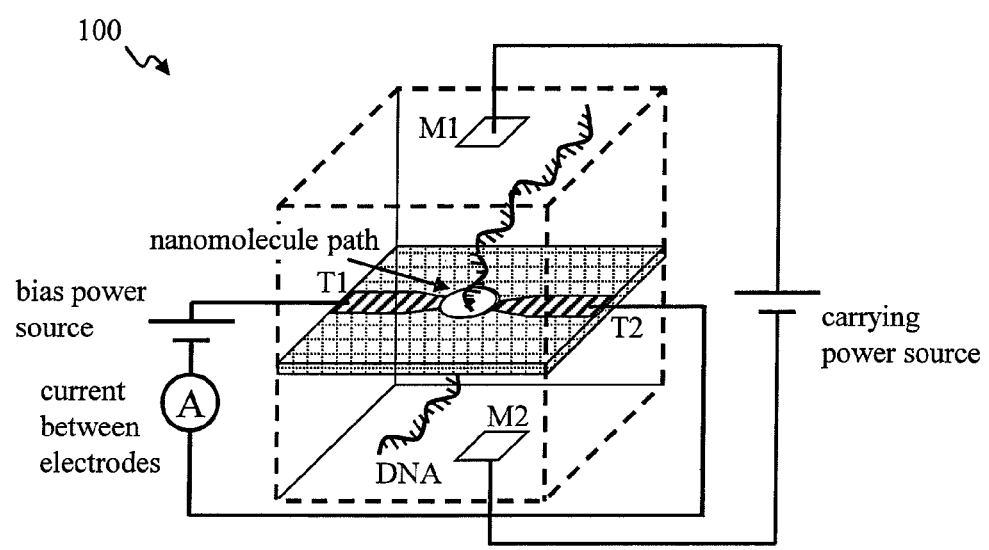
FIG. 47 is a diagram showing a positional relationship between the nanomolecule path and the electrodes.

FIG. 47 is a diagram showing a positional relationship between the nanomolecule path and the electrodes. The electrodes T1 and T2 for detecting electric currents flowing through the bases are disposed at both sides of the nanomolecule path. A bias power source applying bias voltages for measurement is connected to the electrodes T1 and T2. Electrodes M1 and M2 apply electric fields for DNA chains to pass through the nanomolecule path to move. Although not shown in FIG. 47, electrodes S11, S12, and the like described in the embodiment 11 may be provided for detailed control of DNA chain movement.

FIG. 48 is a diagram in which the nanomolecule path in FIG. 47 is extracted. As shown in FIG. 48 (*b*), multiple of the nanomolecule paths shown in FIG. 48 (*a*) may be provided. By providing multiple nanomolecule paths, it is possible to determine the base arrangement of DNA chains in parallel. It is beneficial in accelerating the processing speed. In the configuration shown in FIG. 48 (*b*), the electrodes M1 and M2 in FIG. 47 may be common for all the nanomolecule paths, may be provided for each of the nanomolecule paths, or may be common for multiple nanomolecule paths.

Figure 49:
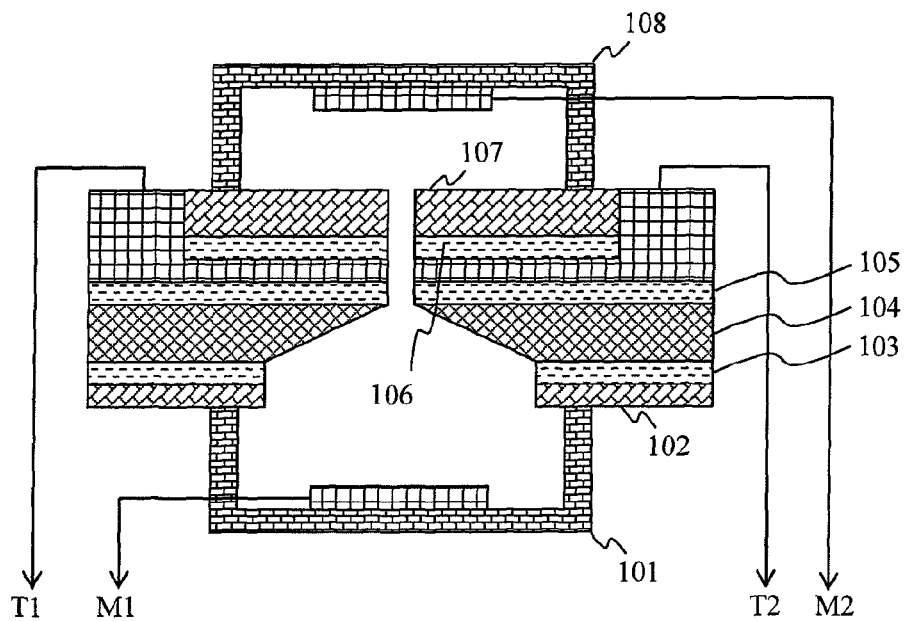
FIG. 49 is a sectional view of the nanomolecule path and the electrode portion shown in FIG. 47.

FIG. 49 is a sectional view of the nanomolecule path and the electrode portion shown in FIG. 47. The containers 101 and 108 contain measured DNA chains and solvents. Electric fields applied to M1 and M2 moves the DNA chains from 101 to 108 or from 108 to 101 through the nanomolecule path. In order to form the electrodes T1 and T2, SiN films 103 and 105 are formed on and beneath a base portion 104 formed with Si, for example. A metal layer forming a part of T1 and T2 is mounted on the upper portion of the SiN film 105. The metal layer is coated with a coat layer 106. The upper portion of the coat layer 106 is coated with a material layer 107 conformal to the apparatus. A part of the coat layer 106 and the material layer 107 is processed to extract the metal layer portion of the electrodes T1 and T2. The lower portion of the SiN film 103 is covered with a coat layer 102.

Figure 50:
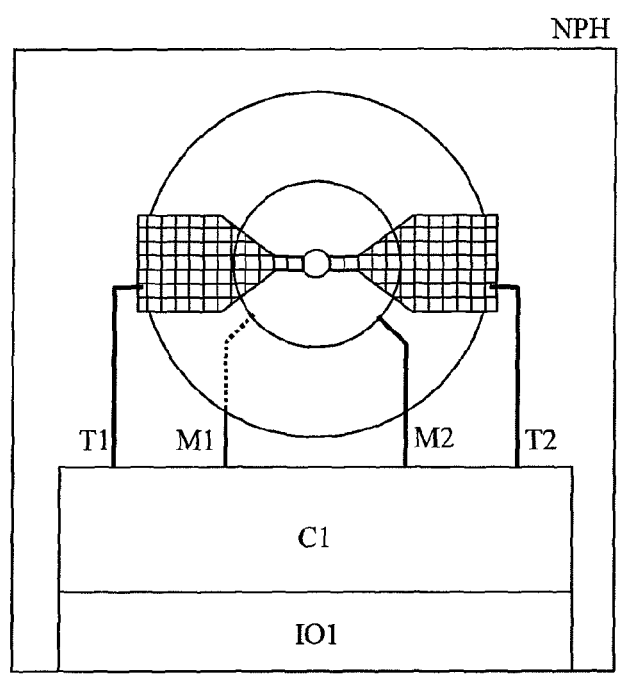
FIG. 50 is a diagram showing a configuration of peripheral devices around the nanomolecule path.

FIG. 50 is a diagram showing a configuration of peripheral devices around the nanomolecule path. The electrodes T1 and T2 and the electrodes M1 and M2 shown in FIG. 49 are connected to a device NPH including a minimum circuit C1 and an interface circuit IO1. The circuit C1 includes the last stage of the bias voltage provided to the electrodes T1 and T2 and its application circuit, a circuit applying voltages to the electrodes M1 and M2 and controlling them, a first stage circuit for detecting electric current flowing between the electrodes T1 and T2, and the like.

FIG. 51 is a diagram showing a configuration of peripheral devices around the device NPH. The device NPH is connected, through an interface, to a device NPB providing the main unit of the biomolecule information analysis apparatus 100. The device NPB is referred to as a head unit of the biomolecule information analysis apparatus 100.

The device NPB includes a circuit LC1 determining the types of bases via an interface IO2. A memory MEM1 stores necessary data. The device NPB is connected to an operation terminal PC via an interface IO3. The operation terminal PC controls the operations of the device NPB and the device NPH via the interface IO3.

FIG. 52 is a diagram showing a configuration example in which the device NPH as the head unit may be removable from the device NPB. In the example shown in FIG. 52, the device NPB may be connected to head units NPH1, NPH2, or NPH 3. Each of the head units NPH1, NPH2, and NPH3 has the same functions. However, they include memories storing IDs that can identify each of the heads. The device NPB or the operation terminal PC can read out the IDs of the head units and can manage them. Since the head units have IDs, after identifying DNA chain bases, it is possible to separate the head units from the device NPB, to clean and retrieve the head units, and to clean and reproduce the head units at places away from the device NPB or discard them. Since the base information of DNA chains is genetic information and is personally unique, the function for removing the head units is significantly important in terms of information protection.

Figure 53:
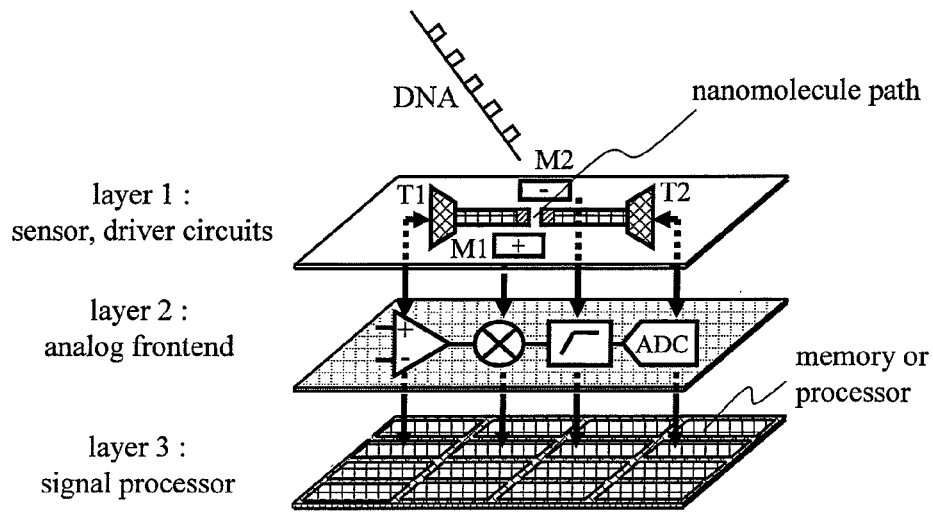
FIG. 53 is a diagram showing a configuration example of a circuit substrate included in the biomolecule information analysis apparatus 100.

FIG. 53 is a diagram showing a configuration example of a circuit substrate included in the biomolecule information analysis apparatus 100. In the configuration shown in FIG. 53, the biomolecule information analysis apparatus 100 includes three layers of a layer 1 to a layer 3. The layer 1 includes a sensor reading electric currents of DNA chains and controlling carriage of DNA chains, a driver electrode, and a control circuit thereof. The layer 2 is a frontend portion including an analog circuit such as integrating and amplifying base electric currents. The layer 3 is a signal processor portion that stores signals from the frontend portion, that controls thresholds for determination, and that converts the signals into data of actual base arrangement. Since these layers have functions independent to some extent from each other, these layers may be implemented on different chips or different circuit substrates, for example. Each of layers is electrically connected.

Figure 54:
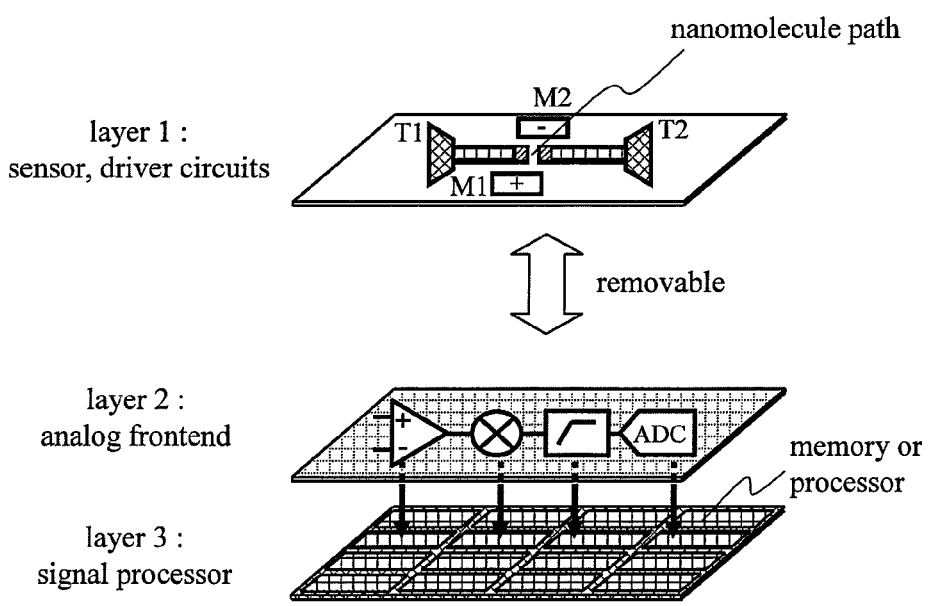
FIG. 54 is a diagram showing an example where each of layers shown in FIG. 53 is removable.

FIG. 54 is a diagram showing an example where each of layers shown in FIG. 53 is removable. In the example shown in FIG. 54, the layer 1 is removable. This enables exchanging the layer 1 at every time when a predetermined number of DNA chain analysis is performed or at every time when analysis for a specific subject is completed. Exchanging each of layers is more cost effective than exchanging whole of the circuit substrate. In addition, since the information of base arrangement of DNA chains is personal information of the person having the DNA, it is possible to prohibit from mixing the information with other person's information. Further, it is possible to retrieve the layer 1 in an institution having a specific equipment to reproduce the layer 1 so that the retrieved layer 1 may be reused.

Figure 55:
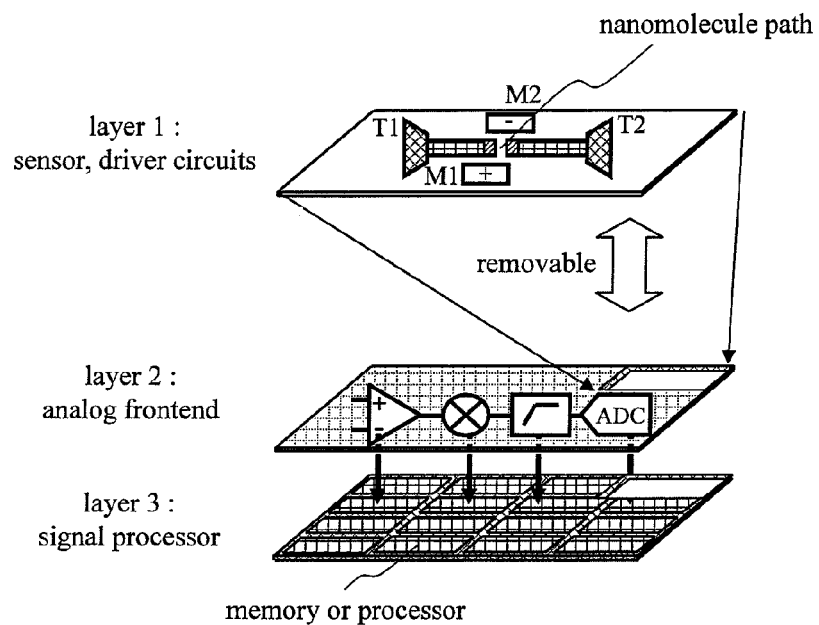
FIG. 55 is a diagram showing another configuration example of the removable portion.

FIG. 55 is a diagram showing another configuration example of the removable portion. Various variations can be assumed for the removable portion. For example, as shown in FIG. 55, the sizes of the three layers are all different and portions for attaching each layer may be provided.

Figure 56:
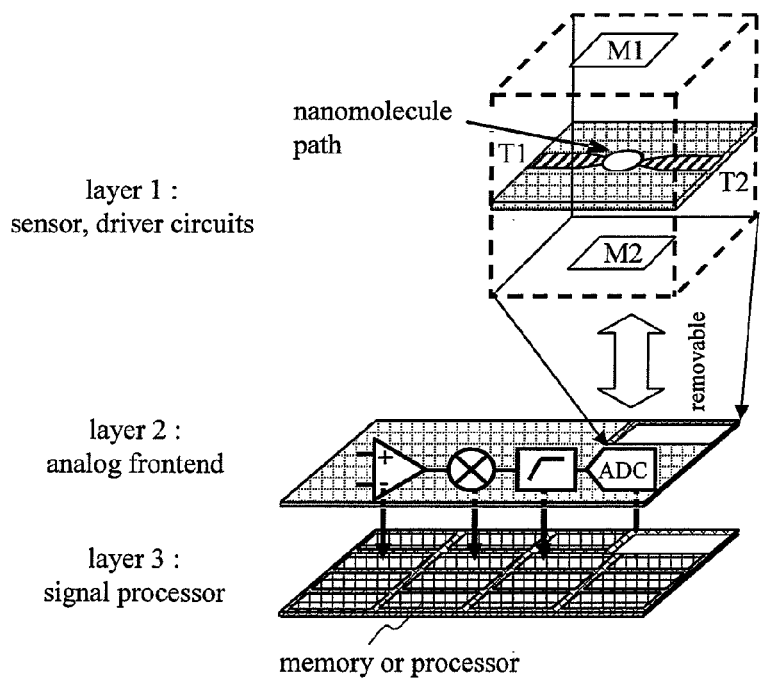
FIG. 56 is a diagram showing a configuration example using a through silicon via (TSV) for electrically connecting each of layers described in FIGS. 53-56.
Figure 58:
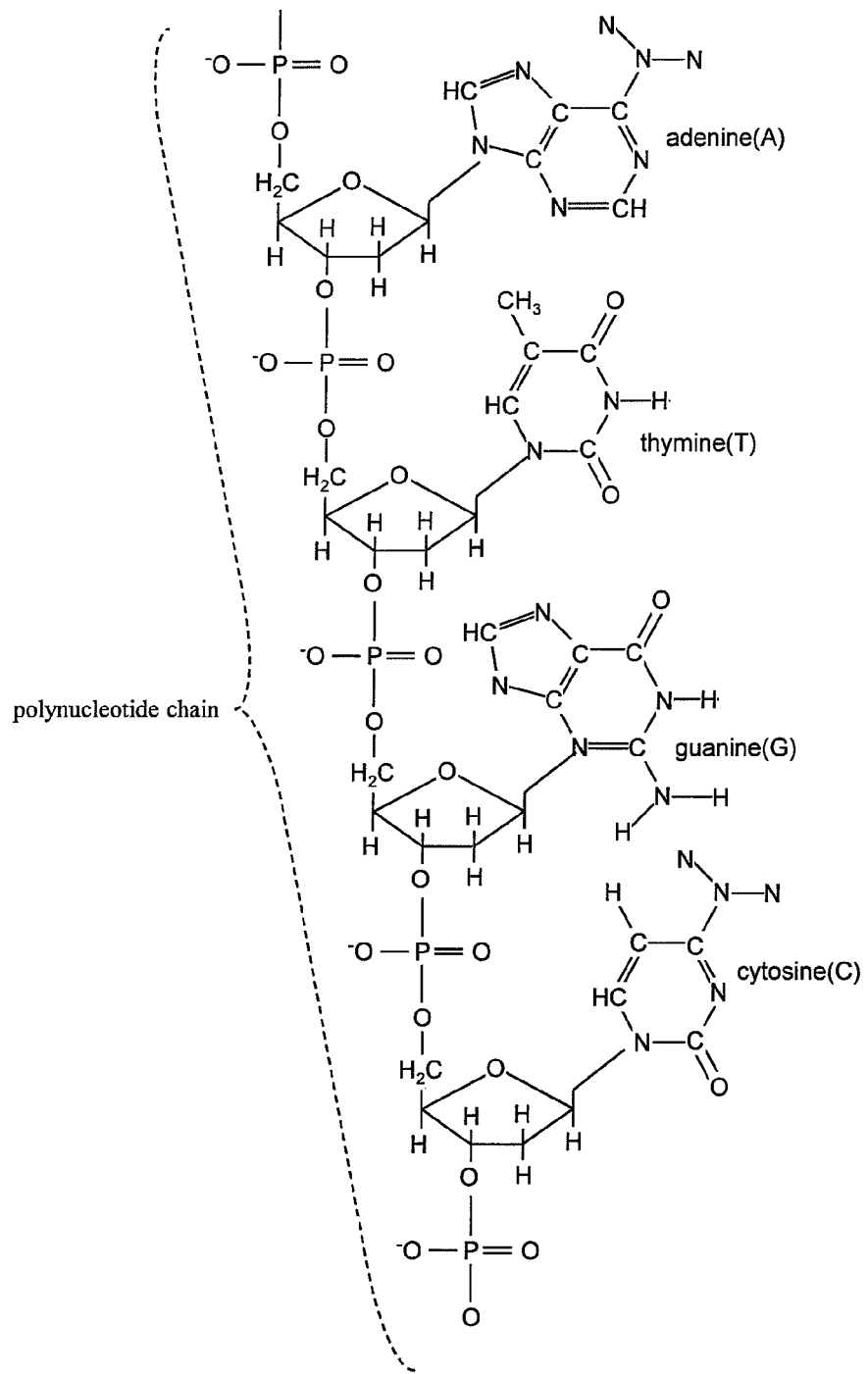
FIG. 58 is a diagram showing a structural example of DNA molecule.
Figure 59:
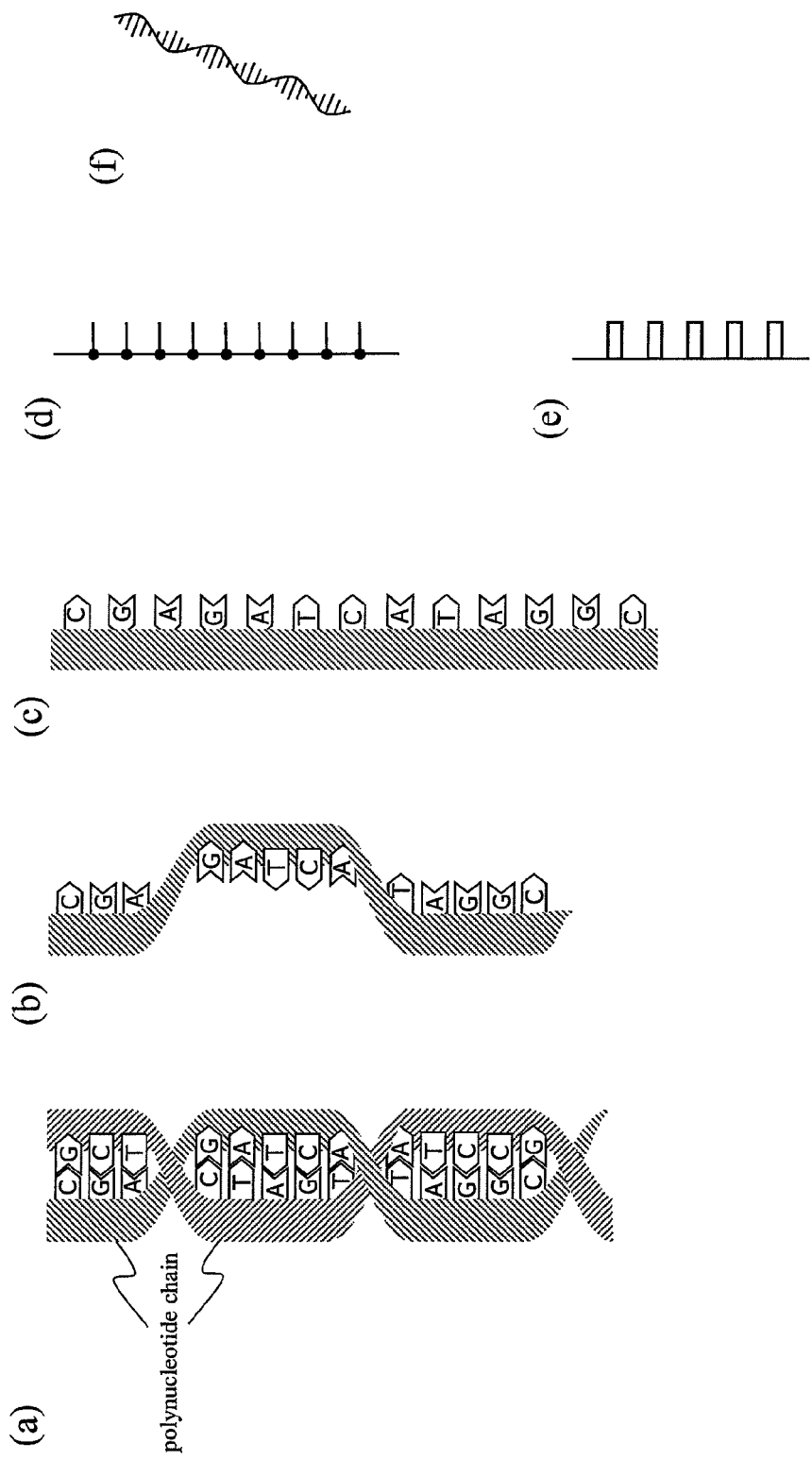
FIG. 59 is a diagram showing a helical structure of a DNA molecule.
Figure 60:
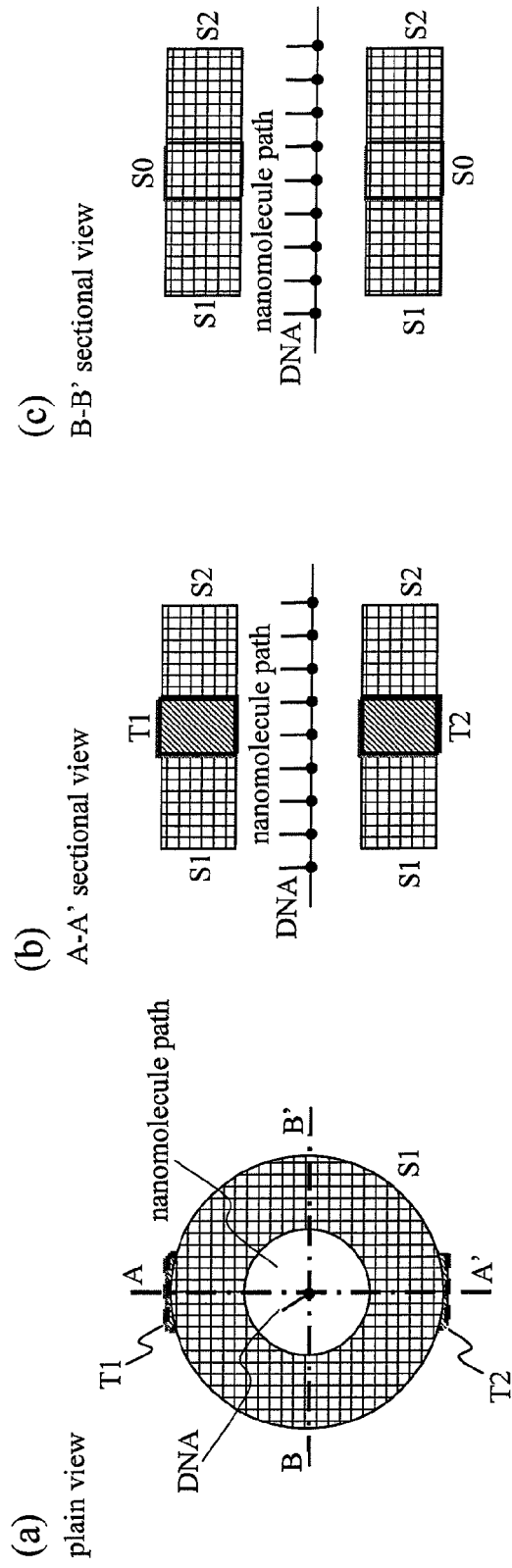
FIG. 60 is a diagram showing a configuration example of a DNA analysis apparatus in which DNAs pass via through holes (nanopores) formed by semiconductor micromachining technique.
Figure 61:
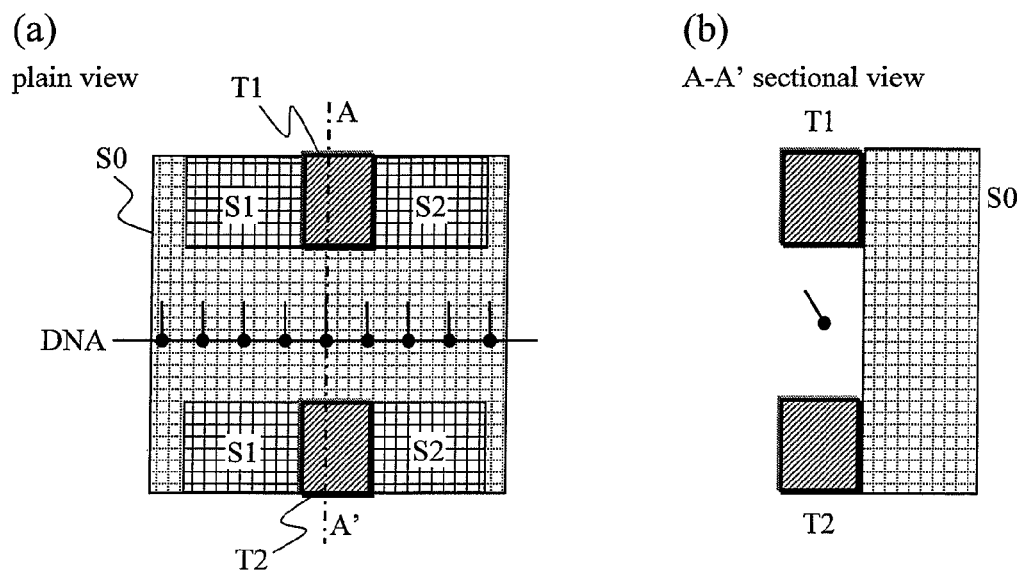
FIG. 61 is a diagram showing a configuration example of a DNA analysis apparatus in which DNAs pass through a small gap (nanogap) formed by semiconductor micromachining technique between the electrodes T1 and T2.

FIG. 56 is a diagram showing a configuration example in which a through hole is used as the nanomolecule path. A shown in FIG. 56, a removable portion in which the layer 2 and the layer 3 are penetrated may be provided.

FIG. 57 is a diagram showing a configuration example using a through silicon via (TSV) for electrically connecting each of layers described in FIGS. 53-56. Using through silicon via reduces the influence from parasitic elements.

FIG. 57 is a diagram showing a configuration of a TSV. FIG. 57 (a-1) is a sectional view of a TSV. FIG. 57 (a-2) is a perspective view. FIG. 57 (a-1) is a A1-A2 sectional view of FIG. 57 (a-2). As shown in these figures, a TSV is formed as an electrical connection portion of metal through a silicon substrate Si.

As shown in FIG. 57 (b), signal current flows between terminals T11, T21, T12, and T22 are performed using TSVs for signal.

FIG. 57 (c) is a diagram showing a configuration example in which TSVs for shielding are arranged surrounding the TSV for signal. This enables reducing the influences of noises from other portions to suppress influences of noises on microcurrents. The TSV for shielding is connected to ground power sources or the like. This configuration reduces the influence of external electromagnetic field on the TSV for signal by the TSV for shielding.

Embodiment 14: Summary

As discussed thus far, the biomolecule information analysis apparatus 100 according to the embodiment 14 uses the nanomolecule path, the circuit for driving the nanomolecule path, and the containers as a head unit, thereby enabling separating the head unit from the signal analyzing portion. By storing IDs in the head units, it is possible to separate the head unit after used, to clean and retrieve it, and to clean and reproduce it at a place away from the device portions or discard the head unit.

REFERENCE SIGNS LIST

T1, T2, T11-T32: electrode for measuring electric current, IT1, integration circuit, CM: determination circuit, SA, SA0-SA2: sense amplifier, VREF: reference electric voltage, OP1: operational amplifier, VPRE: precharge voltage, CPRE: precharge circuit, VOUT: output, PREB: precharge control signal, RVGEN: bias voltage application circuit, VREAD: bias voltage, RV: bias voltage, D1: driver circuit, SA0<0>-SA<2>: sense amplifier output, SE<0:2>: sense amplifier control signal, LOGIC: logic circuit, RO<0>-RO<1>: logic circuit output, S11-S32: base control electrode, A: adenine, T: thymine, G: guanine, C: cytosine

The invention claimed is:

1. A biomolecule information analysis apparatus, comprising:
    a first electrode and a second electrode forming a molecule path configured to permit a biomolecule to pass therethrough;
    an electric voltage application circuit coupled to the first electrode and configured to apply an electric voltage to the first and the second electrodes;
    an integration circuit coupled to the second electrode and configured to accumulate and integrate electrical charges corresponding to an electric current caused to flow from the second electrode by application of the electric voltage from the electric voltage application circuit to the first and the second electrodes and the passing of the biomolecule through the molecule path to produce an integrated electric current value, which varies based on a type of a base of DNA of the biomolecule, and which converges to a single accumulated charge value as integration time increases;
    an amplifier coupled to the integration circuit and configured to receive and amplify the integrated electric current value and to output an amplified result; and
    a comparison circuit coupled to the amplifier and the comparison circuit comprising a signal processor that is programmed to control the operation of the integration circuit and the amplifier and to control the integration of the electrical charges corresponding to the electric current caused to flow from the second electrode by application of the electric voltage from the electric voltage application circuit to the first and the second electrodes and the passing of the biomolecule through the molecule path to produce the integrated electric current value, which converges to a single accumulated charge value as integration time increases, and to identify a structure of the biomolecule by comparing the amplified result with at least one predetermined reference value.

2. The biomolecule information analysis apparatus according to claim 1, wherein the signal processor is further programmed to control:
    the integration circuit to output a plurality of integration results that are different for each type of molecule constructing the biomolecule after a predetermined duration has passed from starting the integration; and
    the comparison circuit to acquire the integration result of the integration circuit at a time point after the predetermined duration has passed from when the integration circuit started the integration, and
    to identify a type of a molecule constructing the biomolecule according to a number of the integration result which exceeds the at least one predetermined reference value.

3. The biomolecule information analysis apparatus according to claim 1,
    wherein the biomolecule is a DNA molecule,
    wherein the molecule path includes a first molecule path configured to permit a chain among two chains forming the DNA molecule to pass and a second molecule path configured to permit another chain among the two chains of the DNA molecule to pass,
    wherein the signal processor is further programmed to control: the integration circuit to perform the integration for each of the DNA molecule passing through the first molecule path and the DNA molecule passing through the second molecule path, and
    the comparison circuit to identify a base of the DNA molecule passing through the first molecule path and a base of the DNA molecule passing through the second molecule path respectively by comparing the integration result of the integration circuit with a corresponding reference value for each of the DNA molecule passing through the first molecule path and the DNA molecule passing through the second molecule path, respectively.

4. The biomolecule information analysis apparatus according to claim 3, wherein the signal processor is further programmed to control: the comparison circuit to identify a base of the DNA molecule passing through any one of the first or the second molecule path and then identify another base by specifying a base which is a complementary pair of the identified base.

5. The biomolecule information analysis apparatus according to claim 1, wherein the signal processor is further programmed to control: the amplifier that comprises a logarithm conversion circuit to output an electric voltage value proportional to a logarithm of the integration result of the integration circuit, and
the comparison circuit to compare an output of the logarithm conversion circuit with the at least one predetermined reference value.

6. The biomolecule information analysis apparatus according to claim 1, further comprising a capacitor that connects the first and the second electrodes with the integration circuit by a capacitive coupling.

7. The biomolecule information analysis apparatus according to claim 1, further comprising:
a memory coupled to and configured to store the integration result of the integration circuit; and
a circuit configured to adjust the reference value using the integration result stored in the memory.

8. The biomolecule information analysis apparatus according to claim 1, further comprising a calibration circuit coupled to and configured to calibrate electric currents outputted from the first and the second electrodes,
wherein the signal processor is further programmed to control: the integration circuit to perform the integration before the biomolecule passes through the molecule path, and to store the integration result into a memory, and the calibration circuit to calibrate, using the integration result stored in the memory, the integration result performed by the integration circuit after the biomolecule passes through the molecule path.

9. The biomolecule information analysis apparatus according to claim 1, further comprising:
a third electrode and a fourth electrode forming the molecule path in conjunction with the first and the second electrodes; and
a control circuit coupled to the third and the fourth electrodes,
wherein the signal processor is further programmed to control the control circuit to adjust an electric field applied to the biomolecule passing through the molecule path by adjusting an electric voltage applied to the third and the fourth electrodes, and to control a motion of the biomolecule within the molecule path using the adjusted electric field.

10. The biomolecule information analysis apparatus according to claim 1, wherein: a plurality of the first and the second electrodes are disposed along the molecule path; and at least one of an electrode pair formed by the first and the second electrodes is different in thickness from other pair of the first and the second electrodes.

11. The biomolecule information analysis apparatus according to claim 1, wherein: a material reacting to the biomolecule passing through the molecule path is attached to the first and the second electrodes.

12. The biomolecule information analysis apparatus according to claim 11, wherein: a plurality of the first and the second electrodes are disposed along the molecule path; and the material attached to at least one of electrode pairs formed by the first and the second electrodes is different from the material attached to other pair of the first and the second electrodes.

13. The biomolecule information analysis apparatus according to claim 1, wherein: a molecule path substrate on which the first and the electrodes are formed is configured to be removable from the biomolecule information analysis apparatus.

14. The biomolecule information analysis apparatus according to claim 13, wherein the signal processor is further programmed to control a storage unit to store an identifier identifying a molecule path substrate on which the first and the second electrodes are formed.

15. The biomolecule information analysis apparatus according to claim 1, wherein: the biomolecule is any one of DNA bases coupled in a form of chain.

* * * * *